(12) United States Patent
Foxlin

(10) Patent No.: US 7,395,181 B2
(45) Date of Patent: **\*Jul. 1, 2008**

(54) MOTION TRACKING SYSTEM

(75) Inventor: Eric M. Foxlin, Arlington, MA (US)

(73) Assignee: Massachusetts Institute of Technology, Cambridge, MA (US)

( \* ) Notice: Subject to any disclaimer, the term of this patent is extended or adjusted under 35 U.S.C. 154(b) by 943 days.

This patent is subject to a terminal disclaimer.

(21) Appl. No.: 10/747,392

(22) Filed: Dec. 23, 2003

(65) Prior Publication Data

US 2004/0143176 A1 Jul. 22, 2004

Related U.S. Application Data

(63) Continuation of application No. 10/183,975, filed on Jun. 25, 2002, now abandoned, which is a continuation of application No. 09/609,424, filed on Jul. 5, 2000, now Pat. No. 6,409,687, which is a continuation of application No. 09/062,442, filed on Apr. 17, 1998, now Pat. No. 6,176,837.

(51) Int. Cl.
*A61B 5/103* (2006.01)

(52) U.S. Cl. ............... 702/155; 702/150; 702/175; 702/176; 702/177; 702/178; 702/179; 702/180; 73/488; 73/510; 600/595; 600/587; 128/897; 367/117; 367/118

(58) Field of Classification Search .......... 702/150, 702/155, 175–180; 600/595, 587; 703/7; 356/139.03; 367/117–118; 73/488, 503.3, 73/504.3, 510, 514.01
See application file for complete search history.

(56) References Cited

U.S. PATENT DOCUMENTS

| | | | |
|---|---|---|---|
| 3,630,079 A | 12/1971 | Hughes et al. | |
| 4,067,015 A | 1/1978 | Mogavero et al. | |
| 4,315,326 A | 2/1982 | Chase, Jr. | |
| 4,408,488 A | 10/1983 | Marshall | |
| 4,807,202 A | 2/1989 | Cherri et al. | |
| 4,928,263 A | 5/1990 | Armstrong et al. | |
| 5,086,404 A \* | 2/1992 | Claussen | 356/139.03 |
| 5,089,972 A | 2/1992 | Nachman et al. | |
| 5,231,483 A | 7/1993 | Sieber et al. | |
| 5,279,309 A | 1/1994 | Taylor et al. | |
| 5,412,619 A | 5/1995 | Bauer | |
| 5,491,670 A | 2/1996 | Weber | |
| 5,495,427 A | 2/1996 | Puma et al. | |
| 5,561,519 A | 10/1996 | Parker et al. | |
| 5,592,401 A | 1/1997 | Kramer | |
| 5,615,132 A \* | 3/1997 | Horton et al. | 703/7 |
| 5,645,077 A | 7/1997 | Foxlin | |
| 5,730,129 A | 3/1998 | Darrow et al. | |
| 5,807,284 A | 9/1998 | Foxlin | |
| 6,176,837 B1 \* | 1/2001 | Foxlin | 600/595 |

OTHER PUBLICATIONS

Foxlin et al. "Minature 6-DOF Inertial System for TRacking HMD's" SPIE, vol. 3362 (Apr. 1998) p. 214-228.\*
Brittan, "Knowing Where Your Head Is At", Technology Review, Feb./Mar. 1995.
Foxlin, "Inertial Head-Tracker Sensor Fusion . . . ", Proc. VRAIS 1996.

(Continued)

*Primary Examiner*—John E. Barlow, Jr.
*Assistant Examiner*—Sujoy K Kundu
(74) *Attorney, Agent, or Firm*—Fish & Richardson P.C.

(57) ABSTRACT

Tracking a motion of a body by obtaining two types of measurements associated with the motion of the body, one of the types including acoustic measurement. An estimate of either an orientation or a position of the body is updated based on one of the two types of measurement, for example based on inertial measurement. The estimate is then updated based on the other of the two types of measurements, for example based on acoustic ranging. The invention also features determining range measurement to selected reference devices that are fixed in the environment of the body.

15 Claims, 16 Drawing Sheets

OTHER PUBLICATIONS

Hollands, "Sourceless Trackers", Technology Review, 4:23-27, 1995.
Sowizral et al., "Tracking Position and Orientation . . . ". IEEE, p. 132-139, 1993.
Angularis VR-360 Inertial Tracking System Brochure, Nov. 1995.
InterSense IS-300 Precision Motion Tracker Brochure, 1996.
Proposal for tracking system, Oct. 1996.
InterSense IS-600 Precision Motion Tracker Brochure, May 1997.
InterSense IS-900CT Camera Tracker Brochure, Jul. 1997.
Bhatnagar, D., "Position Trackers for Head Mounted Display Systesm: A survey", XP-002276242, p. 1-21, Mar. 29, 2003.
Foxlin et al., "Miniature 6-DOF inertial system for tracking HMDs", XP002943637, SPIE Conference on Helmut- and Head-Mounted Displays III, SPIE vol. 3362 (Apr. 1998), p. 214-228.
Meyer, et al., "A Survey of Position Trackers", XP-002103552, Presence, vol. 1, No. 2, Spring 1992, p. 173-200.

* cited by examiner

MOTION TRACKING SYSTEM

This application is a continuation and claims the benefit of priority under 35 USC 120 of U.S. application Ser. No. 10/183,975, filed Jun. 25, 2002, now abandoned which is a continuation of Ser. No. 09/609,424, filed Jul. 5, 2000 and issued as U.S. Pat. No. 6,409,687 on Jun. 25, 2002, which is a continuation of U.S. application Ser. No. 09/062,442, filed Apr. 17, 1998 and issued as U.S. Pat. No. 6,176,837 on Jan. 23, 2001.

BACKGROUND

The invention relates to motion tracking.

Motion tracking can use a variety of measurement modes, including inertial and acoustic measurement modes, to determine the location and orientation of a body.

Inertial motion tracking is based on measuring linear acceleration and angular velocity about a set of typically orthogonal axes. In one approach, multiple spinning gyroscopes generate forces proportional to the rates at which their spinning axes rotate in response to rotation of a tracked body to which the gyroscopes are attached. These forces are measured and used to estimate angular velocity of the body. Micro-machined vibrating elements and optical waveguide based devices may be used in place of gyroscopes.

Accelerometers generate signals proportional to forces which result from linear acceleration. In an inertial tracking system, the angular velocity and acceleration signals are integrated to determine linear velocity, linear displacement, and total angles of rotation.

As the signals generated by gyroscopic devices are noisy, the integration process results in accumulation of noise components, which is generally known as "drift". Miniaturized and low cost gyroscopic devices typically exhibit greater error. Drift rates can be as high as several degrees per second for a body at rest, and several degrees for every rotation of the body by 90 degrees. Errors in orientation estimates also affect location estimation as the estimated orientation of the body is used to transform acceleration measurements into the fixed reference frame of the environment prior to their integration. Inaccuracy in this transformation can result in gravity appearing as a bias to resulting horizontal acceleration measurements.

One way to correct drift is to use additional sensors, such as inclinometers and a compass to occasionally or continually correct the drift of the integrated inertial measurements. For instance, U.S. Pat. No. 5,645,077, issued to Eric M. Foxlin on Jul. 8, 1997, discloses such an approach. This patent in incorporated herein by reference.

Another approach to motion tracking uses acoustic waves to measure distance between one or more points on a body and fixed reference points in the environment. In one arrangement, termed an "outside-in" arrangement, a set of acoustic emitters at the fixed points on the body emit pulses that are received by a set of microphones at the fixed reference points in the environment. The time of flight from an emitter to a microphone is proportional to an estimate of the distance between the emitter and the microphone (i.e., the range). The range estimates from the emitters to the respective microphones are used to triangulate the location of the emitters. The locations of multiple emitters on the body are combined to estimate the orientation of the body.

Other measurement modes, such as optical tracking of light sources on a body, can also be used to track motion of the body.

SUMMARY

In one aspect, in general, the invention is a method for tracking a motion of a body which includes obtaining two types of measurements associated with the motion of the body, one of the types comprising acoustic measurement, updating an estimate of either an orientation or a position of the body based on one of the two types of measurement, for example based on inertial measurement, and updating the estimate based on the other of the two types of measurements, for example based on acoustic ranging.

In another aspect, in general, the invention is a method for tracking the motion of a body including selecting one of a set of reference devices, transmitting a control signal to the selected reference device, for example by transmitting a wireless control signal, receiving a range measurement signal from the reference device, accepting a range measurement related to a distance to the selected reference device, and updating a location estimate or an orientation estimate of the body using the accepted range measurement. The method can further include determining a range measurement based on a time of flight of the range measurement signal.

Advantages of the invention include providing a 6-degree-of-freedom tracking capability that can function over an essentially unlimited space in which an expandable constellation of ultrasonic beacons is installed. Inertial measurements provide smooth and responsive sensing of motion while the ultrasonic measurements provide ongoing correction of errors, such as those caused by drift of the inertial tracking component of the system. Small and inexpensive inertial sensors, which often exhibit relatively large drift, can be used while still providing an overall system without unbounded drift. Small, lightweight inertial sensors are well suited for head mounted tracking for virtual or augmented reality display systems. By correcting drift using ultrasonic measurements, drift correction measurements which may be sensitive to external factors such as magnetic field variations, are not needed. The constellation of ultrasonic beacons can be easily expanded as each beacon functions independently and there is no need for wiring among the beacons. The tracking device only relies on use of a small number of ultrasonic beacons at any time, thereby allowing the space in which the tracking device operates to have irregular regions, such as multiple rooms in a building.

Another advantage of the invention is that by using an "inside-out" configuration, there is no latency in acoustic range measurements due to motion of the body after an acoustic wave is emitted.

Yet another advantage of the invention is that tracking continues using inertial measurements even when acoustic measurements cannot be made, for example, due to occlusion of the beacons. Drift in the inertial tracking is then corrected once acoustic measurements can once again be made.

In yet another advantage, the invention provides line-of-sight redundancy whereby one or more paths between emitters and sensors can be blocked while still allowing tracking of a body.

Other features and advantages of the invention will be apparent from the following description, and from the claims.

DESCRIPTION

Figure 1:
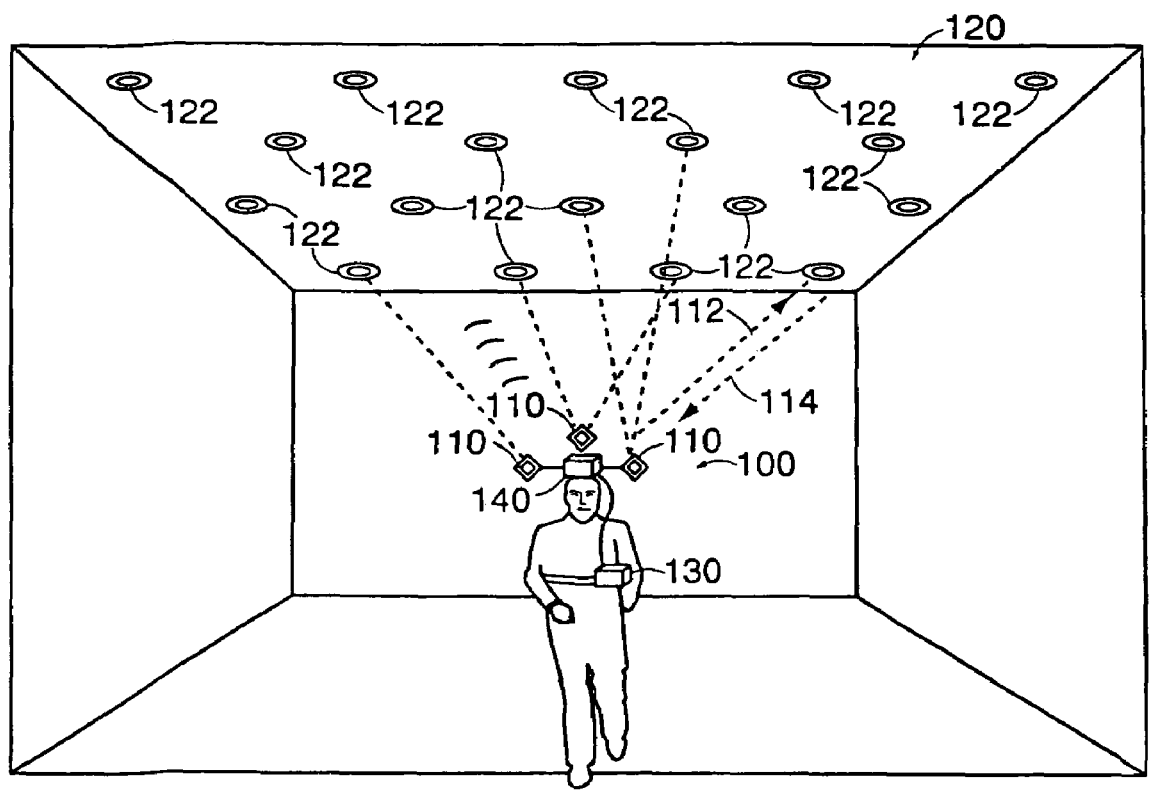
FIG. 1 shows a tracking device and a constellation of acoustic beacons used for tracking the device.

Referring to FIG. 1, a tracking device 100 which maintains an estimate of its location and orientation is free to move within a large room. For example, tracking device 100 can be fixed to a head-up display (HUD) on an operator's head, and tracking device 100 moves through the room, and changes orientation, as the operator moves and orients his head. Tracking device 100 includes a processor 130 coupled to an inertial measurement unit (IMU) 140 which provides inertial measurements related to linear acceleration and to rates of rotation. Processor 130 uses the inertial measurements to determine motion of tracking device 100 as it moves through the room.

Processor 130 is also coupled to an array of three ultrasonic range measurement units (URM) 110 which are used to receive acoustic signals sent from an ultrasonic beacon array 120, a "constellation" of beacons. Ultrasonic beacon array 120 includes independent ultrasonic beacons 122 in fixed locations in the environment, for example, arranged on the ceiling of the large room in a regular pattern such as on a grid with 2 foot spacing. Processor 130 uses the signals from particular ultrasonic beacons 122, as well as known three-dimensional locations of those beacons, to estimate the range to those beacons and thereby sense motion for tracking device 100. Each ultrasonic beacon 122 sends an ultrasonic pulse 114 in response to infra-red command signal 112 sent from tracking device 100. In particular, each URM 110 on tracking device 100 broadcasts infra-red (IR) signals to all of the ultrasonic beacons 122. These IR signals include address information so that only one beacon, or a small number of beacons, recognize each IR signal as intended for it, and responds to the signal. In response to an IR signal, an addressed beacon immediately broadcasts an ultrasonic pulse that is then received by one or more URM 110. As processor 130 knows that the addressed beacon responded immediately to the IR command, it determines the time of flight by measuring the delay from issuing the IR command to detecting the ultrasonic pulse. The time of flight of the ultrasonic pulse is used to estimate the range to the beacon, which is then used to update the position and orientation of tracking device 100.

Both the inertial measurements and the ultrasonic signal based measurements have limitations. Relying on either mode of measurement individually is not as accurate as combining the measurements. Tracking device 100 combines measurements from both measurement modes and adjusts its estimate of position and orientation (i.e., 6 degrees of freedom, "6-DOF") to reflect measurements from both modes as they are available, or after some delay. To do this, processor 130 hosts an implementation of an extended Kalman filter (EKF) that is used to combine the measurements and maintain ongoing estimates of location and orientation of tracking device 100, as well as to maintain an estimate of the uncertainty in those estimates.

Figure 2:
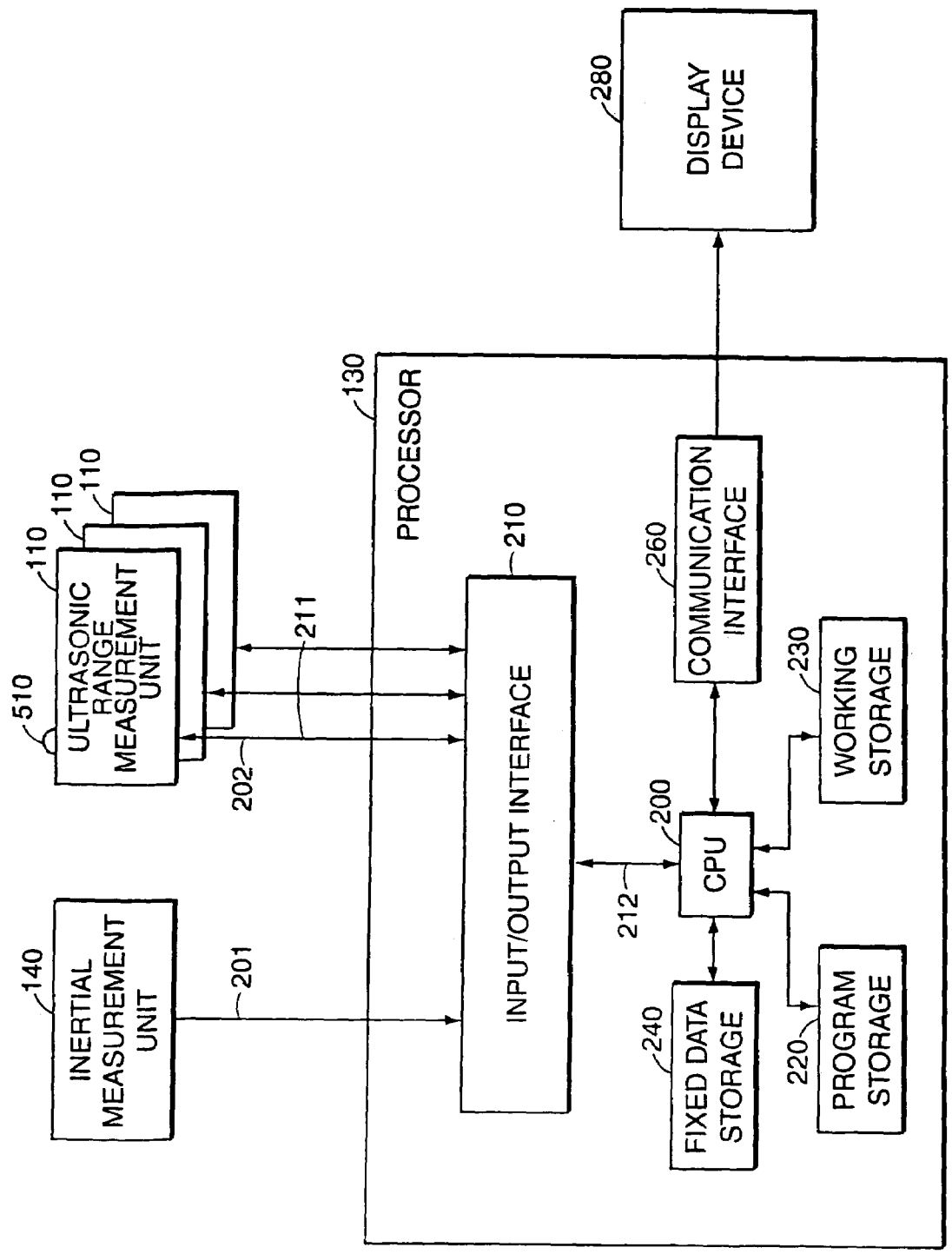
FIG. 2 shows components of a tracking device processor.

Referring to FIG. 2, processor 130 includes a central processing unit (CPU) 200, such as an Intel 80486 microprocessor, program storage 220, such as read-only memory (ROM), and working storage 230, such as dynamic random-access memory (RAM). CPU 200 is also coupled to an input/output interface 210 which provide an interface to IMU 140 and the URM 110. Input/output interface 210 includes digital logic that provides digital interfaces to IMU 140 and the URM 110.

IMU 140 provides a serial data stream 201 encoding inertial measurements. Input/output interface 210 converts this serial data to a parallel form 212 for transfer to CPU 200. Each URM 110 accepts a serial signal 211 that is used to drive an IR light emitting diode 510 to broadcast the IR control signals to ultrasonic beacons 122 (FIG. 1). Input/output interface 210 accepts address information from CPU 200 identifying one or more ultrasonic beacons and provides the serial signal to each of the URM 110 which then impose the serial signal on an IR transmission (e.g., by amplitude modulation). The same serial signal is provided to all the URMs 110, which concurrently broadcast the same IR signal. Each URM 110 provides in return a logical signal 202 to input/output interface 210 indicating arrivals of ultrasonic pulses. Input/output interface 210 includes timers that determine the time of flight of ultrasonic pulses from the beacons, and thereby determines range estimates to the beacons. These range estimates are provided to CPU 200.

An implementation of a tracking algorithm is stored in program storage 220 and executed by CPU 200 to convert the measurements obtained from input/output interface 210 into position and orientation estimates. CPU 200 is also coupled to fixed data storage 240, which includes information such as a predetermined map of the locations of the ultrasonic beacons, and the locations of the microphones of the URM 110. Processor 130 also includes a communication interface 260 for coupling CPU 200 with other devices, such as a display device 280 that modifies its display based on the position and orientation of tracking device 100.

Figure 3:
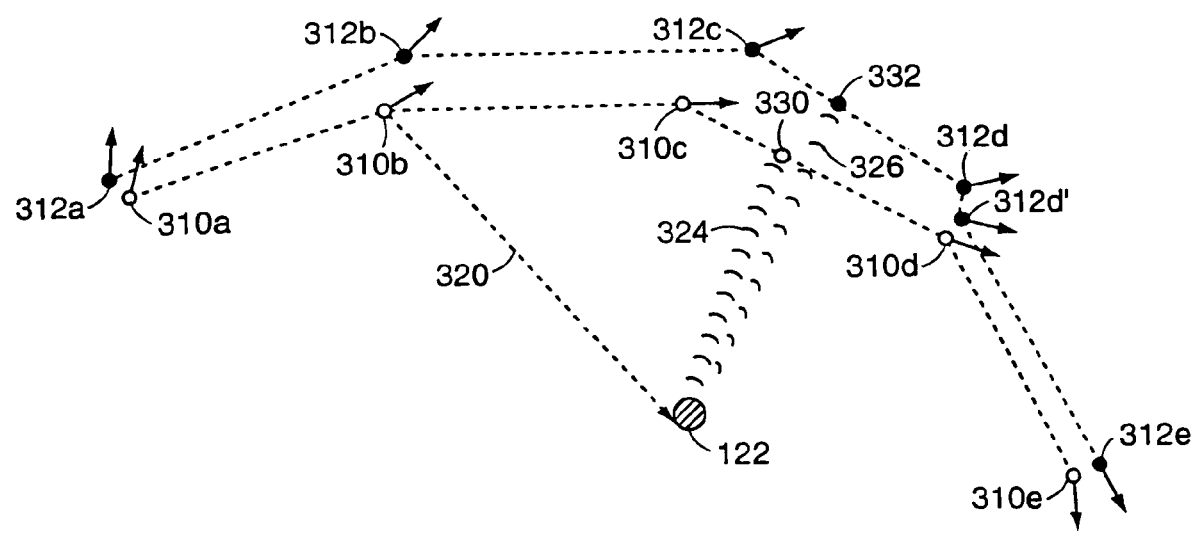
FIG. 3 illustrates a combined inertial and acoustic tracking approach.

Operation of the system can be understood by referring to FIG. 3, a two-dimensional view of the room shown in FIG. 1 (from above). The sequence of open circles and arrows 310a-e represent the actual location and orientation of tracking device 100 at each of a sequence of time steps. Based on prior measurements, and on inertial measurements at the first time step, filled circle and arrow 312a represent the estimate by tracking device 100 of the location and orientation of the tracking device at the first time step. At the next time step, tracking device 100 moves to position 310b, and based on a new inertial measurement, tracking device 100 updates its position estimate to 312b. This is repeated for the next time step with actual position 310c and estimated position 312c.

After reaching position 310b, tracking device 100 sends an IR command addressed one one of the ultrasonic transducers 122, illustrated by dotted line 320. After receiving the IR command (with essentially no delay), ultrasonic transducer 122 transmits an ultrasonic pulse, illustrated by wave 324. Wave 324 reaches tracking device 100 some time later, at actual location 330. Based on the time of arrival, tracking device 100 estimates that it was at position 332 when wave 326 reached it.

At the next time step, tracking device 100 first estimates its position 312d based on an inertial measurement. Using range information related to the separation of the location of ultrasonic transducer 122 and location 332 and a measured time of flight of the ultrasonic wave, tracking device 100 computes a refined position estimate 312d'. The process repeats using inertial measurements at true position 310e and estimated position 312e.

In general, both an inertial measurement and an ultrasonic measurement can be used at each time step, although ultrasonic measurement can be made less frequently. At each time step, both location and orientation (attitude) is updated. The ultrasonic pulses can provide information related to both location and orientation through the use of multiple microphones that are displaced relative to one another.

Figure 4:
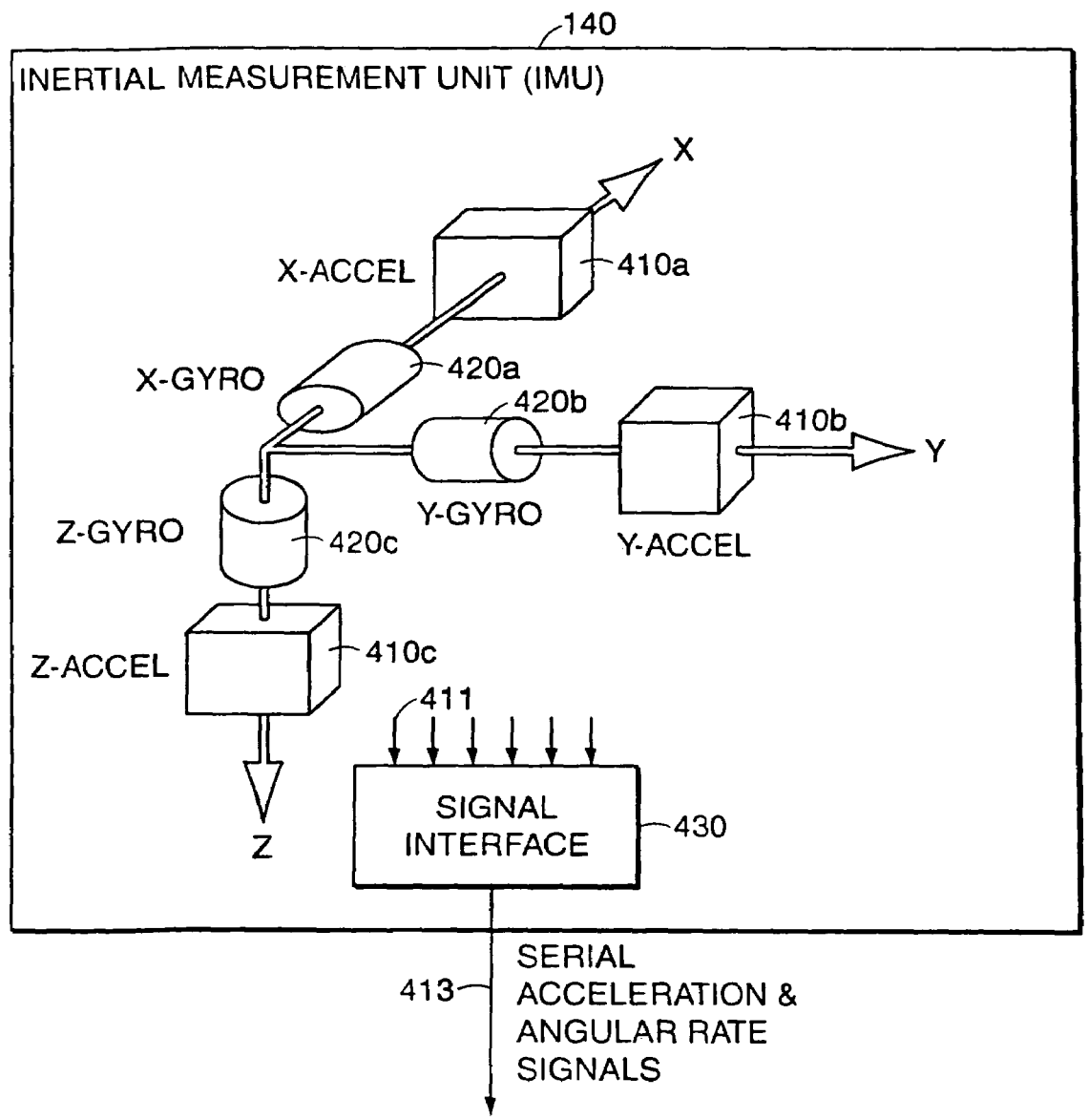
FIG. 4 shows an inertial measurement unit (IMU)

Referring to FIG. 4, inertial measurement unit (IMU) 140 includes three angular rate sensors (e.g., micro-machined vibrating rotation sensors or small rotating gyroscopes) 420a-c, and three linear acceleration sensors 410a-c. The sensors are arranged to lie along three orthogonal axes that remain fixed in the frame of reference of tracking device 100. Each acceleration sensor provides a signal that is generally proportional to the acceleration along the corresponding axis, and each angular rate sensor provides a signal that is generally proportional to the rate of rotation about the corresponding axis.

As the orientation of inertial measurement unit 140 changes, the signals such as the acceleration signals correspond to changing directions in the fixed (navigation) reference frame of the room. Inertial measurement unit 140 also includes a signal interface 430 which accepts the signals 411 from each of the six accelerometers and angular rate sensors, and transmits a serial data stream 413 which multiplexes digital representations of the acceleration and angular rate signals. As is discussed further below, the acceleration and angular rate signals are imperfect, and may exhibit additive bias and scaling inaccuracies. These scaling and bias inaccuracies may depend on the motion of the device.

Figure 5:
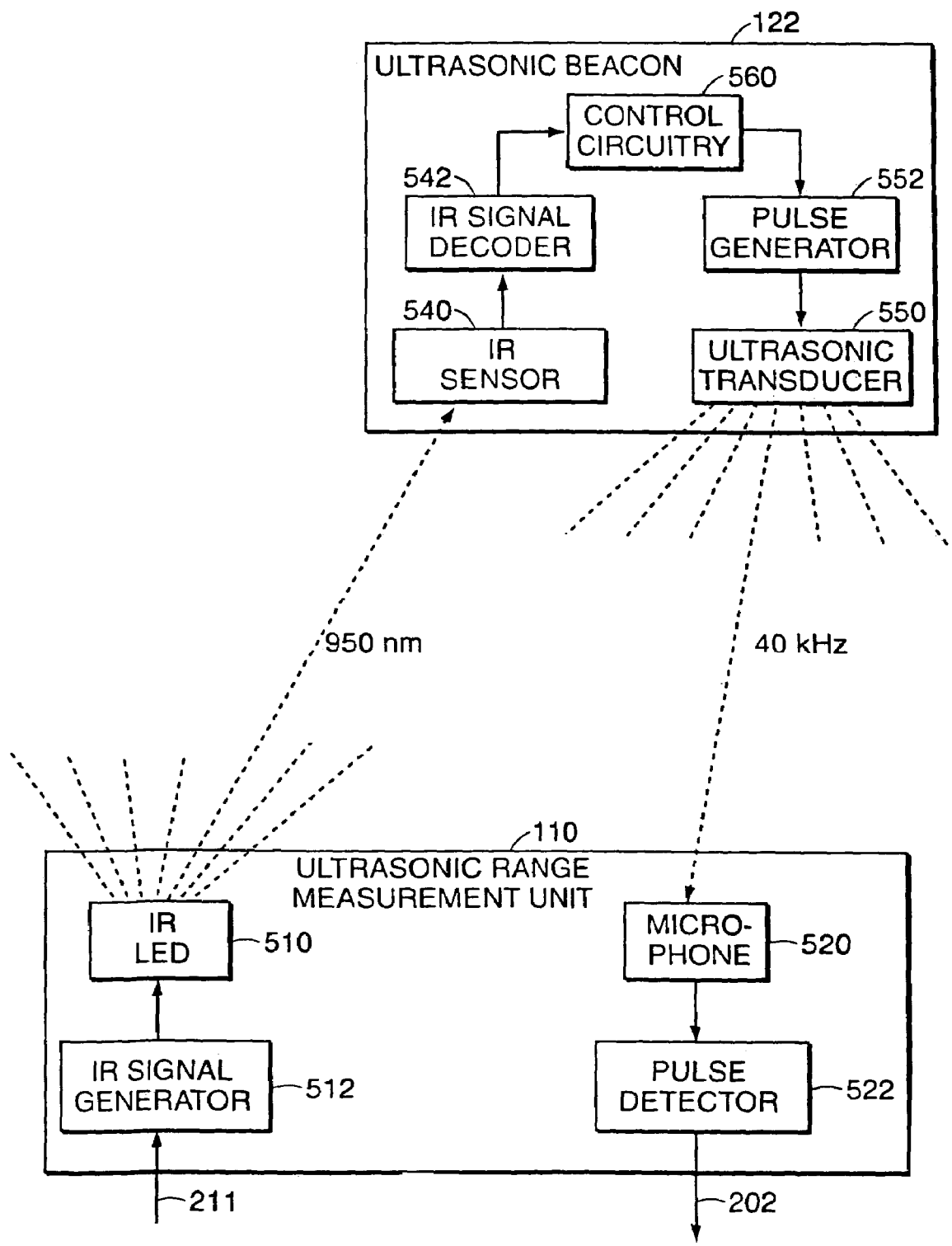
FIG. 5 shows an ultrasonic range measurement unit (URM) and an ultrasonic beacon.

Referring to FIG. 5, each ultrasonic measurement unit 110 includes an infra-red (IR) light-emitting diode (LED) 510 that is driven by IR signal generator 512. Signal generator 512 accepts serial signal 211 from input/output interface 210 (FIG. 2) and drives IR LED 510 to transmit that signal to one or more ultrasonic beacon 122. The address of an ultrasonic beacon to which arrange is desired is encoded in serial signal 211. Each ultrasonic beacon 122 includes an IR sensor 540 which, if there is a sufficiently short unobstructed path between ultrasonic range measurement unit 110 and that ultrasonic beacon, receives the IR signal which is then decoded by IR signal decoder 542. This decoded signal includes the address information transmitted by the ultrasonic range measurement unit. Control circuitry 560 receives the decoded IR signal, and determines whether that ultrasonic beacon is indeed being addressed, and if so, signals a pulse generator 552 to provide a signal to an ultrasonic transducer 550 which generates an ultrasonic pulse. The pulse passes through the air to ultrasonic range measurement unit 110 where a microphone 520 receives the ultrasonic pulse and passes a corresponding electrical signal to a pulse detector 522 which produces a logical signal indicating arrival of the pulse. This pulse detection signal is passed to input/output interface 210 (FIG. 2). As discussed below, the time of flight is not a perfectly accurate measurement of range. Error sources include timing errors in detection of the pulse, acoustic propagation rate variations, for example due to air temperature or air flow, and non-uniform in different directions propagation of the ultrasonic wave from the ultrasonic beacon.

Figure 6:
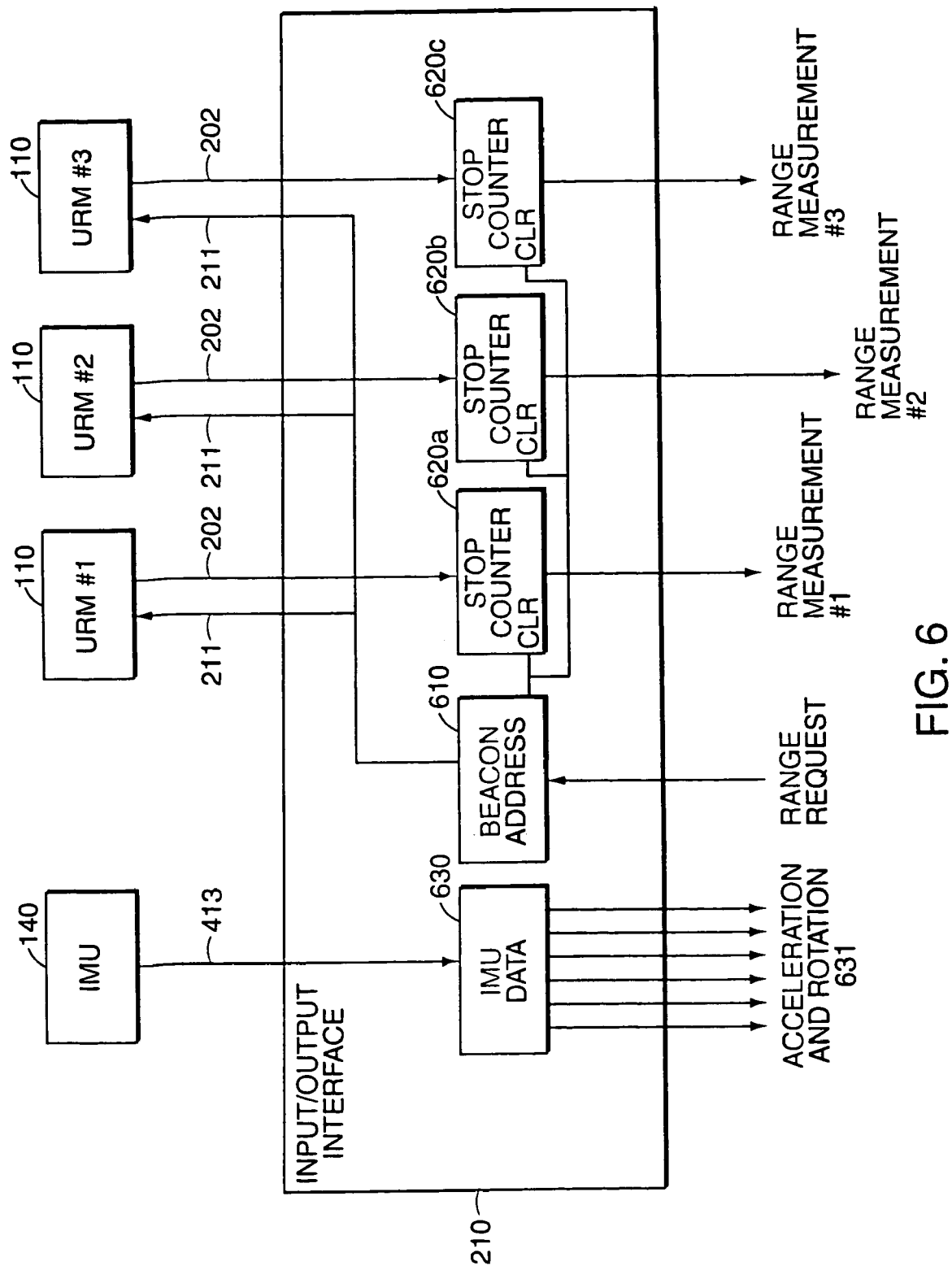
FIG. 6 shows an input/output interface used in a tracking device processor to interface with inertial and ultrasonic measurement units.

Input/output interface 210 includes circuitry (i.e., a programmable logic array) which implements logical components shown in FIG. 6. An IMU data buffer 630 accepts serially encoded acceleration and angular rate data 413 from IMU 140, and provides the six acceleration and rotation measurements 631 as output to CPU 200. Input/output interface 210 also includes a beacon address buffer 610. CPU 200 (FIG. 2) provides an address of the ultrasonic beacon to which a range should be measured. Beacon address buffer 610 stores the address and provides that address in serial form to each of the URMs 110. At the same time that the address is transmitted by each of the URM 110 (and received by the ultrasonic beacons 122), three counters 620a-c are reset and begin incrementing from zero at a fixed clocking rate (e.g., 2 MHz). When each URM 110 detects the ultrasonic pulse from the beacon, the corresponding pulse detection signal is passed to the corresponding counter which stops counting. The counts are then available to CPU 200 as the measurements of the time of flight of the ultrasonic pulse from the ultrasonic beacon to each URM 110.

Figure 7A:
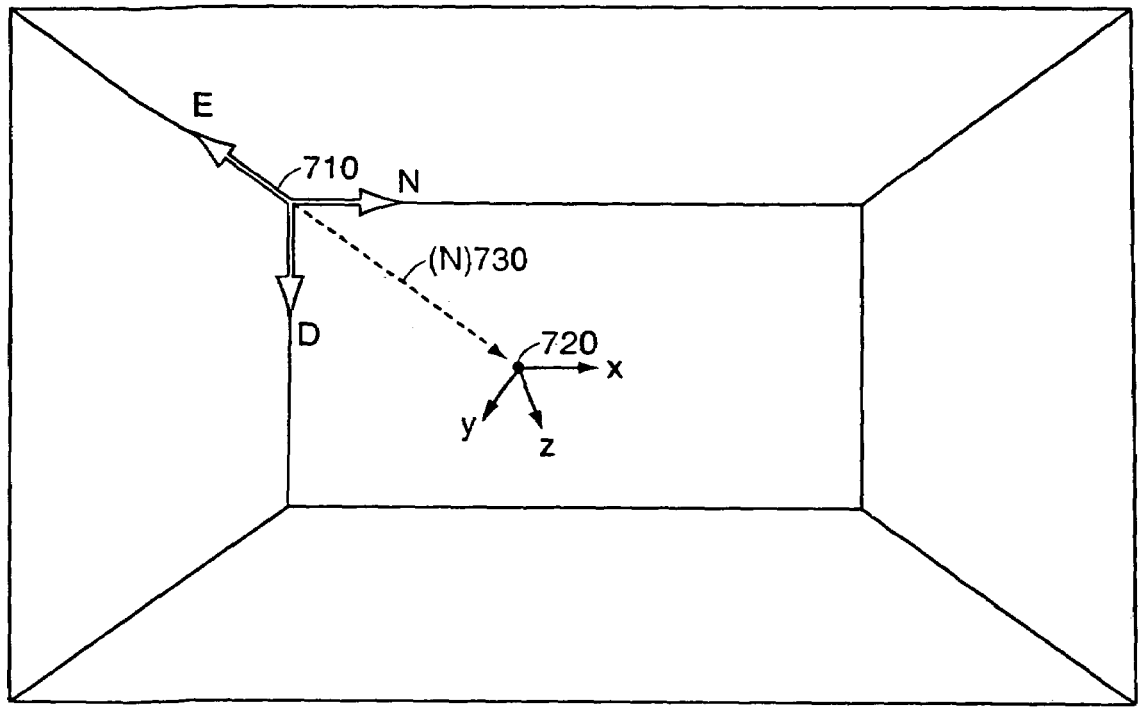
FIG. 7a illustrates the navigation and body frames of reference.
Figure 7B:
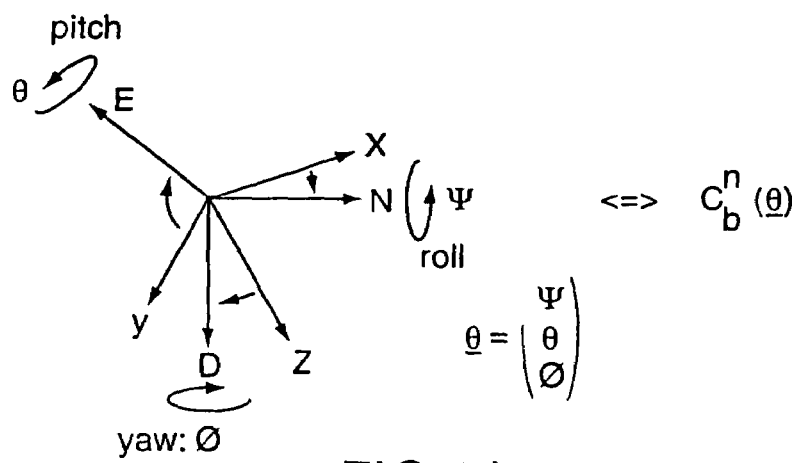
FIG. 7b illustrates mutual tracking devices.

Referring to FIGS. 7a-b, tracking device 100 (FIG. 1) determines its location in the navigation reference frame of the room, shown as axes 710, labeled N (north), E (east), and D (down). Location $r^{(n)}$ 730 is a vector with components $(r_N^{(n)}, r_E^{(n)}, r_D^{(n)})^T$ of the displacement from axes 710 in the N, E, and D directions respectively. Tracking device 100 also determines its attitude (orientation).

Referring to FIG. 7b, attitude is represented in terms of the roll, pitch, and yaw (Euler) angles, $\theta = (\psi, \theta, \phi)^T$, needed to align the body attitude, represented by coordinate axes 720, with the navigation attitude represented by coordinate axes 710. The three Euler angles are represented as a 3×3 direction cosine matrix, $C_b^n(\theta)$, which transforms a vector of coordinates in the body frame of reference by essentially applying in sequence yaw, pitch, and then roll motions around the z, y, and then x axes. The direction cosine matrix can be defined as $$C(\theta) = \begin{bmatrix} 1 & 0 & 0 \\ 0 & \cos\psi & -\sin\psi \\ 0 & \sin\psi & \cos\psi \end{bmatrix} \begin{bmatrix} \cos\theta & 0 & -\sin\theta \\ 0 & 1 & 0 \\ \sin\theta & 0 & \cos\theta \end{bmatrix} \begin{bmatrix} \cos\phi & -\sin\phi & 0 \\ \sin\phi & \cos\phi & 0 \\ 0 & 0 & 1 \end{bmatrix}$$

The superscript and subscript notation $C_b^n$ signifies that the matrix takes a vector in the "b" (body) reference frame and provides a vector in the "n" (navigation) reference frame.

Figure 8:
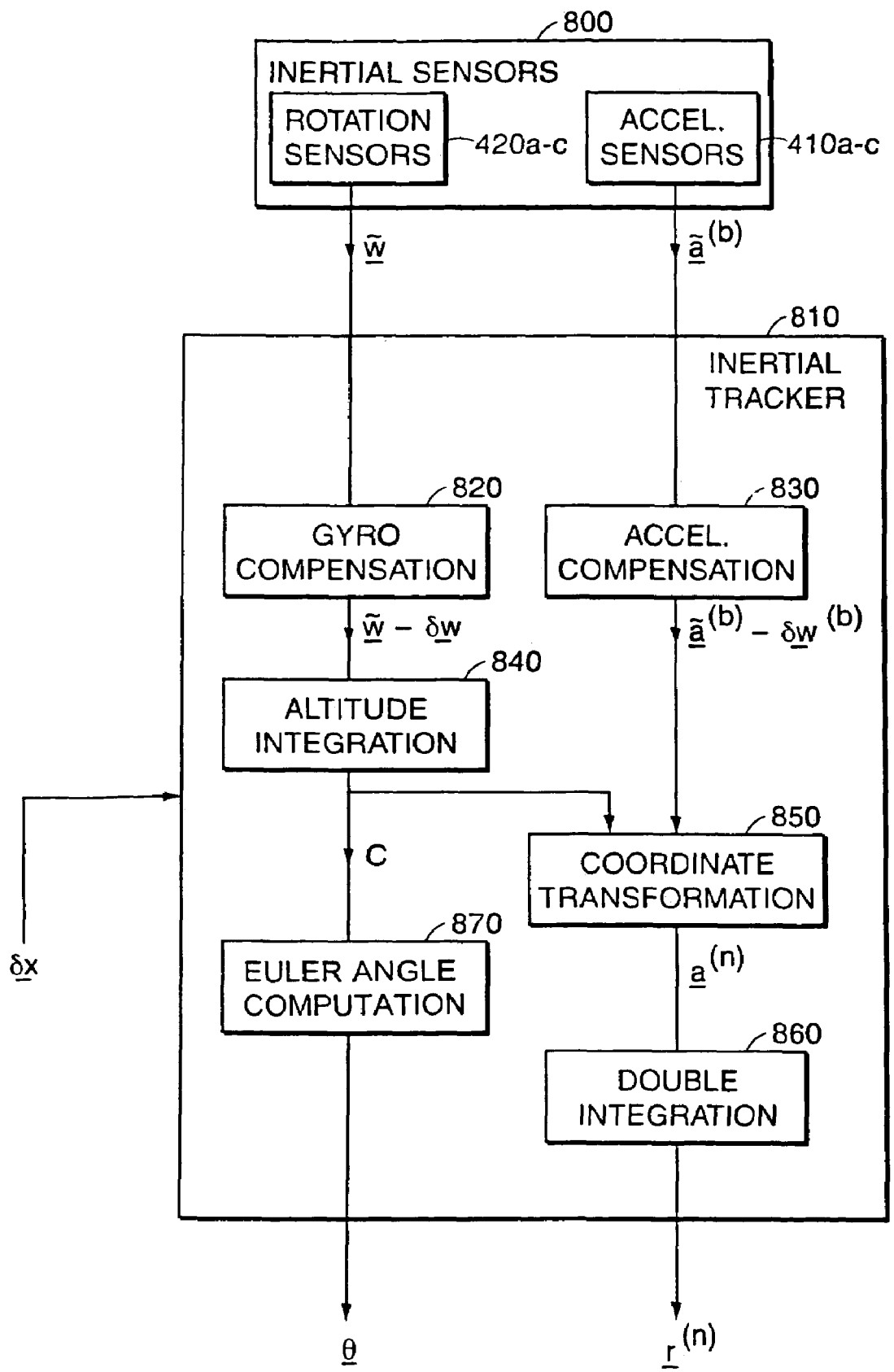
FIG. 8 is a signal flow diagram of an inertial tracker.

Referring to FIG. 8, inertial sensors 800, including rotation sensors 420a-c and acceleration sensors 410a-c, provide inertial measurement signals to an inertial tracker 810. Inertial tracker 810 implements a discrete time approximation of the signal flow shown in the FIG. 8. Inertial tracker 810 includes several stages. First, gyroscope compensation 820 modifies the (vector) angular rate signal $\omega$ to account for bias in the measurement. In this example, only an additive bias $\delta\omega$ is corrected. Other biases such as a multiplicative error (e.g., an incorrect scale factor), and errors due to mounting inaccuracies can be corrected as well. Accelerometer compensation 830 similarly corrects for an additive bias $\delta a^{(b)}$ on the acceleration signals $a^{(b)}$. As is discussed fully below, several parameters, including the bias terms $\underline{\delta\omega}$ and $\underline{\delta a}^{(b)}$, are estimated using ultrasonic measurements.

Attitude integration 840 updates the attitude estimate based on the bias corrected rotation signal. In this example, attitude integration is performed using a direction cosine representation of the attitude. A discrete time implementation of the continuous differential equation $\dot{C}_b{}^n(t) = C_b{}^n(t) \, S(\omega(t))$ is used to update the direction cosine matrix at a fixed rate, typically between 100 and 200 per second. Changing notation to a discrete time system (e.g., $C_k = C_b{}^n(k\Delta t)$), the discrete time update of the direction cosine matrix is implemented as $$C_k = C_{k-1}\left(I + \frac{\sin\delta\theta}{\delta\theta} S(\underline{\delta\theta}) + \frac{1-\cos\delta\theta}{\delta\theta^2} S(\underline{\delta\theta})^2\right)$$

where $$\underline{\delta\theta} = \frac{\underline{\omega}_{k-1} + \underline{\omega}_k}{2}\Delta t, \; \delta\theta = \|\underline{\delta\theta}\|$$

and $$S(\underline{\delta\theta}) = \begin{bmatrix} 0 & -\delta\theta_z & \delta\theta_y \\ \delta\theta_z & 0 & -\delta\theta_x \\ -\delta\theta_y & \delta\theta_x & 0 \end{bmatrix}$$

is the skew symmetric matrix of $\underline{\delta\theta}$. Note that $S(\underline{\delta\Theta})$ satisfies $$S(\underline{\delta\theta})^2 = \delta\theta^2 I - \underline{\delta\theta}\,\underline{\delta\theta}^T.$$

In order to ensure that $C_k$ truly is a direction cosine matrix, its rows are orthonormalized after each iteration to remove any numerical or approximation errors that may have entered into its entries.

Based on the tracked direction cosine matrix $C_k$, coordinate transformation 850 accepts the bias corrected acceleration signal in the body reference frame and outputs an acceleration signal in the navigation reference frame according to $$\underline{a}_k^{(n)} = C_k(\underline{\tilde{a}}_k^{(b)} - \underline{\delta a}_k^{(b)}) + (0,0,-g)^T.$$

Double integration 860 then computes the velocity and position according to $$\underline{v}_k^{(n)} = \underline{v}_{k-1}^{(n)} + \frac{a_{k-1}^{(n)} + a_k^{(n)}}{2}\Delta t, \text{ and}$$

$$\underline{r}_k^{(n)} = \underline{r}_{k-1}^{(n)} + \underline{v}_{k-1}^{(n)}\Delta t + \frac{2a_{k-1}^{(n)} + a_k^{(n)}}{6}\Delta t^2.$$

Euler angle computation 870 takes the direction cosine matrix and outputs the corresponding Euler angles. The output of inertial tracker 810 is $(\theta, r^{(n)})^T$. The state of the inertial tracker includes a 15-dimensional vector composed on five sets of three-dimensional values $$\underline{x} = (\underline{\theta}, \underline{\omega}, \underline{r}^{(n)}, \underline{v}^{(n)}, \underline{a}^{(n)})^T.$$

As is discussed fully below, inertial tracker 810 receives error update signals $\delta\underline{x}$ derived from ultrasonic range measurements that it uses to correct the attitude, velocity, and position values, and to update the parameters of the gyroscope and accelerometer bias correction elements.

Figure 9:
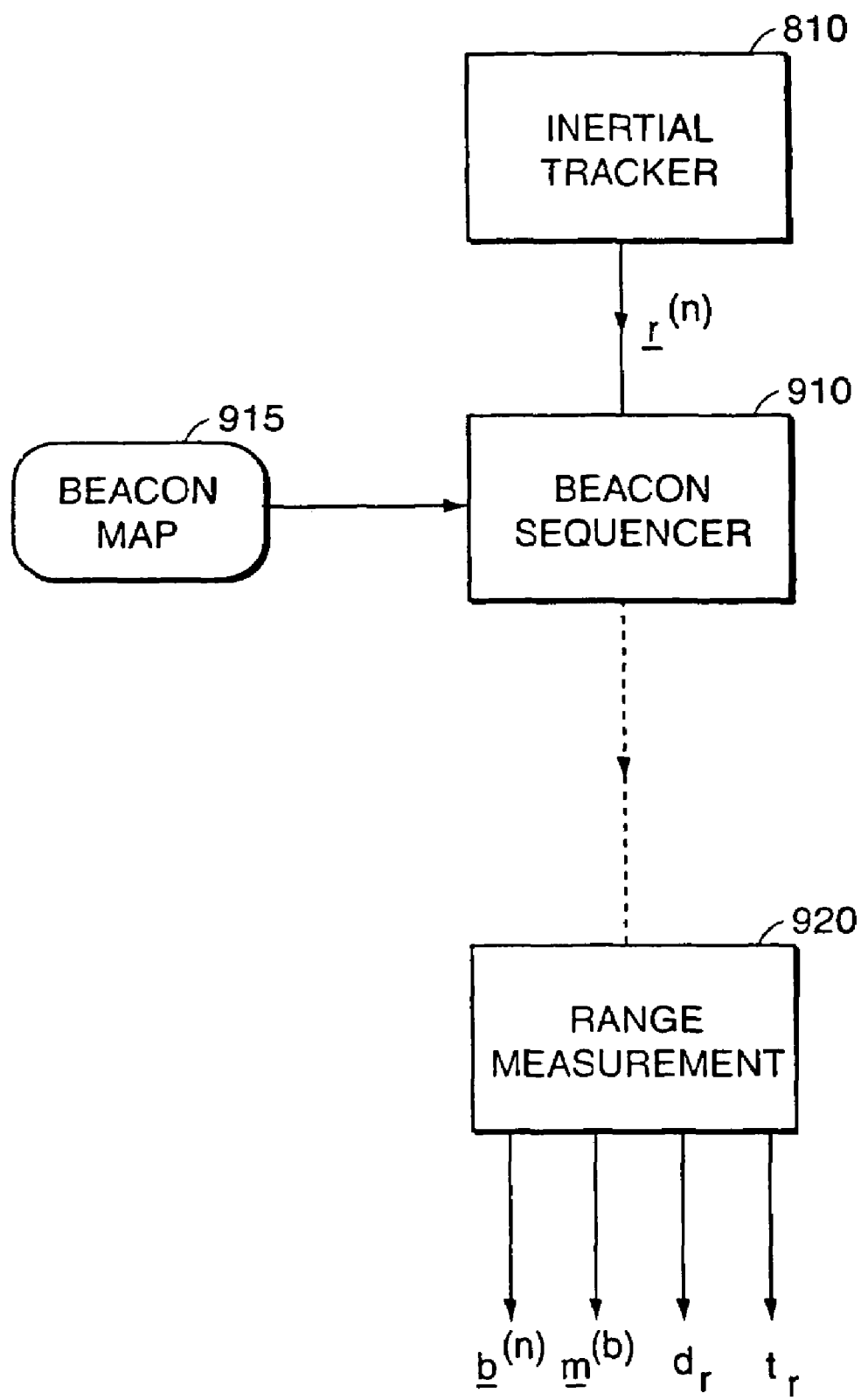
FIG. 9 is a signal flow diagram of an ultrasonic range measurement subsystem.

Referring to FIG. 9, a beacon sequencer 910 receives location estimates $r^{(n)}$ from inertial tracker 810. Using a beacon map 915 of the locations (and addresses) of the ultrasonic beacons 122 (shown in FIG. 1), beacon sequencer 910 determines which beacon to trigger at each time step in order to generate ultrasonic range measurements. For instance, beacon sequencer 910 determines the closest beacons to the current location, and cycles among these beacons on each time step. As the location estimate changes, the set of closest beacons also, in general, changes. After beacon sequencer 910 triggers each of the beacons in turn, the corresponding ultrasonic pulses arrive and are detected by the tracking device. Each pulse generates one range measurement for each microphone used to detect the pulse. In this embodiment, each pulse generates a set of three range measurements, one from each of the microphones in the three URM 110.

Referring still to FIG. 9, range measurement 920 corresponds to the process of receiving an ultrasonic range estimate. The relevant parameters for a range measurement are the location of the addressed beacon, $\underline{b}^{(n)}$, the location of the microphone used to detect the pulse, $\underline{m}^{(b)}$, the range estimate itself, $d_r$, and the time the pulse was detected, $t_r$, which is used to correct for latency in the measurements. Note that if the location estimate had no error, and the range estimate was perfectly accurate, then the range estimate would satisfy $$d_r = \|\underline{b}^{(n)} - (\underline{r}^{(n)}(t_r) + C_b{}^n(t_r)\underline{m}^{(b)})\|.$$

Deviations from this equality are used to correct the parameters and outputs of inertial tracker 810.

Figure 10:
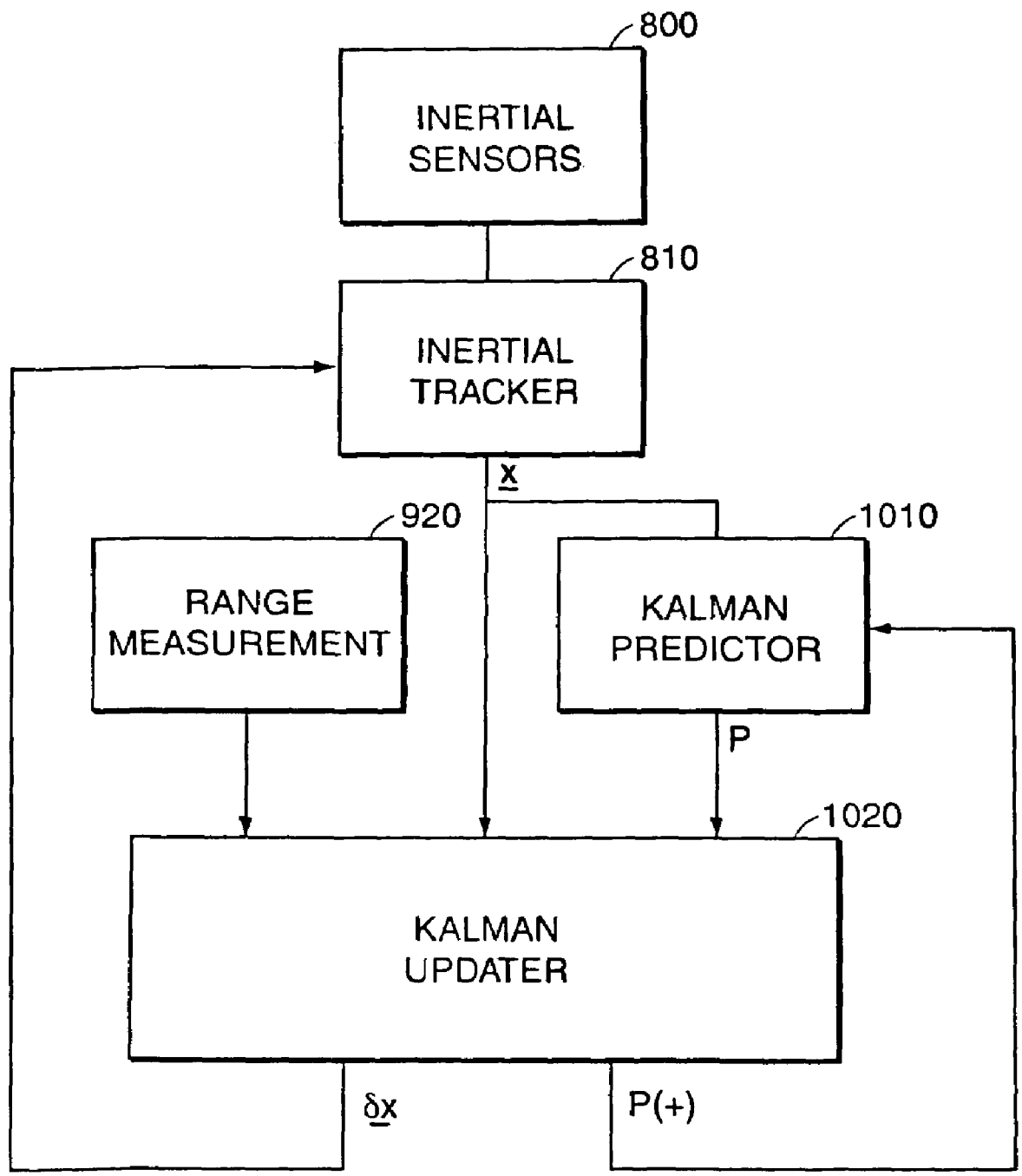
FIG. 10 is a signal flow diagram of a tracking device including an inertial tracker and Kalman predictor and updater elements.

A complementary Kalman filter is used by tracking device 100 to improve the tracked location and orientation estimate by incrementally updating the tracked quantities as the range measurements come in. Referring to FIG. 10, the approach involves two related components. As inertial tracker 810 updates its output x, a Kalman predictor 1010 maintains an estimated covariance matrix P of the error in x. For instance, in the absence of any drift compensation in inertial tracker 810, the covariance matrix P would correspond to an ever increasing error.

The second component used in this approach is a Kalman updater 1020 which accepts information from range measurement 920 and using this measurement information determines an estimate of the accumulated error $\delta x$ which it feeds back to inertial tracker 810 where it is used to update x. Also, after each ultrasonic measurement, Kalman updater 1020 computes a new estimated covariance matrix P(+) of the error in x after the update, which it feeds back to Kalman predictor 1010. Each ultrasonic measurement partially corrects the output of inertial tracker 810. A continuous series of ultrasonic updates ensures that the error remains small.

Inertial tracker 810 is a nonlinear processor of its inputs, and therefore, a formulation of a Kalman filter for a purely linear filter driven by Gaussian noise is not appropriate. Using what is generally known as an "extended Kalman filter" (EKF), a linearized dynamical system model which characterizes the propagation of error in the output x of inertial tracker 810 is used. The error that the EKF models is $$\underline{\delta x} = (\underline{\phi}, \underline{\delta\omega}^{(b)}, \underline{\delta r}^{(n)}, \underline{\delta v}^{(n)}, \underline{\delta a}^{(b)})^T$$

with the components corresponding to the components of the vector output of the inertial tracker. Note that the error term $\delta a^{(b)}$ is modeled in the body coordinate system rather than in the navigation coordinate system, and that the other elements correspond directly to errors in the output of inertial tracker 810. The parameters of the linearized error propagation model include a state transition matrix, and a covariance matrix of a driving noise which is assumed to drive this error model. Both the state transition matrix and the driving noise covariance depend on the output of inertial tracker. In the absence of any measurements, the mean of the error process remains zero. However, the covariance of the error grows. The linearized model of error propagation is $$\underline{\delta x}_k = F(\underline{x}_{k-1})\underline{\delta x}_{k-1} + \underline{w}_{k-1}.$$

The entries of $F_k = F(\underline{x}_{k-1})$ are derived from a perturbation analysis of the update equations used in inertial tracker 810, and correspond to the following error propagation equations:

$$\underline{\phi}_k = \underline{\phi}_{k-1} - C_b^n \underline{\delta\omega}_{k-1},$$

$$\underline{\delta\omega}_k = \underline{\delta\omega}_{k-1},$$

$$\underline{\delta r}_k = \underline{\delta r}_{k-1} + \Delta t \underline{\delta v}_{k-1} - \frac{1}{2}\Delta t^2 \left(C_b^n \underline{\delta a}_{k-1}^{(b)} - S(\underline{\phi}_{k-1})(\underline{a}_{k-1}^{(n)} + (0, 0, -g)^T)\right)$$

$$\underline{\delta v}_k = \underline{\delta v}_{k-1} + \Delta t (\underline{\delta a})_{k-1}^{(b)} - \Delta t S(\underline{\phi}_{k-1})(\underline{a}_{k-1}^{(n)} + (0, 0, -g)^T), \text{ and}$$

$$\underline{\delta a}_k^{(b)} = \underline{\delta a}_{k-1}^{(b)}.$$

The covariance $Q_k$ of the process noise $w_k$ is assumed to be diagonal. The entries of this covariance matrix are derived from known sources of error in the inertial measurements provided to inertial tracker 810, including additive bias errors, scaling errors, alignment errors of the sensors with the body axes, and signal noise from the sensors themselves. The individual variances depend on the output of the inertial tracker as follows:

$$Q_k = \text{diag}(\sigma_{\phi_x}^2, \sigma_{\phi_y}^2, \sigma_{\phi_z}^2, \sigma_\omega^2, \sigma_\omega^2, \sigma_\omega^2, \sigma_{r_x}^2, \sigma_{r_y}^2, \sigma_{r_z}^2, \sigma_{v_x}^2, \sigma_{v_y}^2)$$

where the individual variance terms are parameterized as follows:

$\sigma_{\phi_x}$=GyroScale $\omega_x$ $\Delta t$+GyroAlign($\omega_y$+$\omega_x$) $\Delta t$+GyroNoise$\sqrt{\Delta t}$ $\sigma_{\phi_y}$=GyroScale $\omega_x$ $\Delta t$+GyroAlign($\omega_x$+$\omega_z$) $\Delta t$+GyroNoise$\sqrt{\Delta t}$ $\sigma_{\phi_z}$=GyroScale $\omega_z$ $\Delta t$+GyroAlign($\omega_x$+$\omega_y$) $\Delta t$+GyroNoise$\sqrt{\Delta t}$ $\sigma_\omega$=GyroBiasChangeRate $\Delta t$ $\sigma_{r_x} = \sigma_{r_y} = \sigma_{r_z} = 0$ $\sigma_{v_x}$=AccelScale $a_x$ $\Delta t$+AccelAlign($a_y$+$a_z$) $\Delta t$+AccelNoise$\sqrt{\Delta t}$ $\sigma_{v_y}$=AccelScale $a_y$ $\Delta t$+AccelAlign($a_x$+$a_z$) $\Delta t$+AccelNoise$\sqrt{\Delta t}$ $\sigma_{v_z}$=AccelScale $a_z$ $\Delta t$+AccelAlign($a_x$+$a_y$) $\Delta t$+AccelNoise$\sqrt{\Delta t}$ $\sigma_a^2$=AccelBiasChangeRate $\Delta t$ where GyroScale, AccelScale, GyroAlign, and AccelAlign correspond to degree of uncertainty in calibration coefficients used for instrument error compensation. In general, a non-diagonal process noise covariance can be used.

Figure 11:
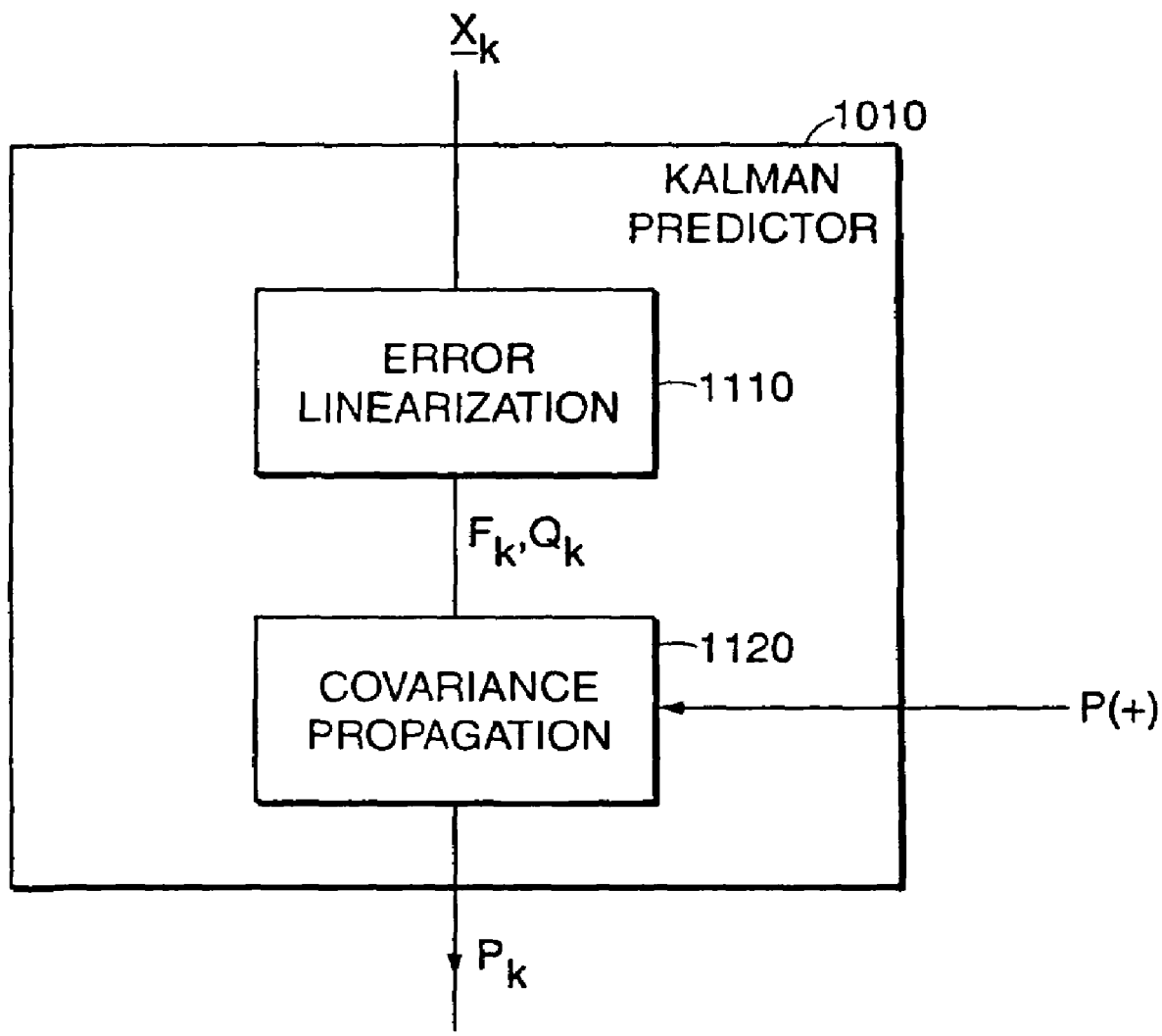
FIG. 11 is a signal flow diagram of a Kalman predictor.

Referring to FIG. 11, Kalman predictor 1010 has two stages. An error linearization stage 1110 first computes $F_k$ and $Q_k$ as outlined above. Then, a covariance propagation stage 1120 iteratively updates the error covariance by applying a Kalman filter covariance propagation equation $$P_k = F_{k-1} P_{k-1} F_{k-1}^T + Q_k$$

on each time step. When Kalman predictor 1010 receives an updated covariance P(+), which is produced as a result of an ultrasonic range measurement, that updated covariance replaces the current error covariance P.

Figure 12:
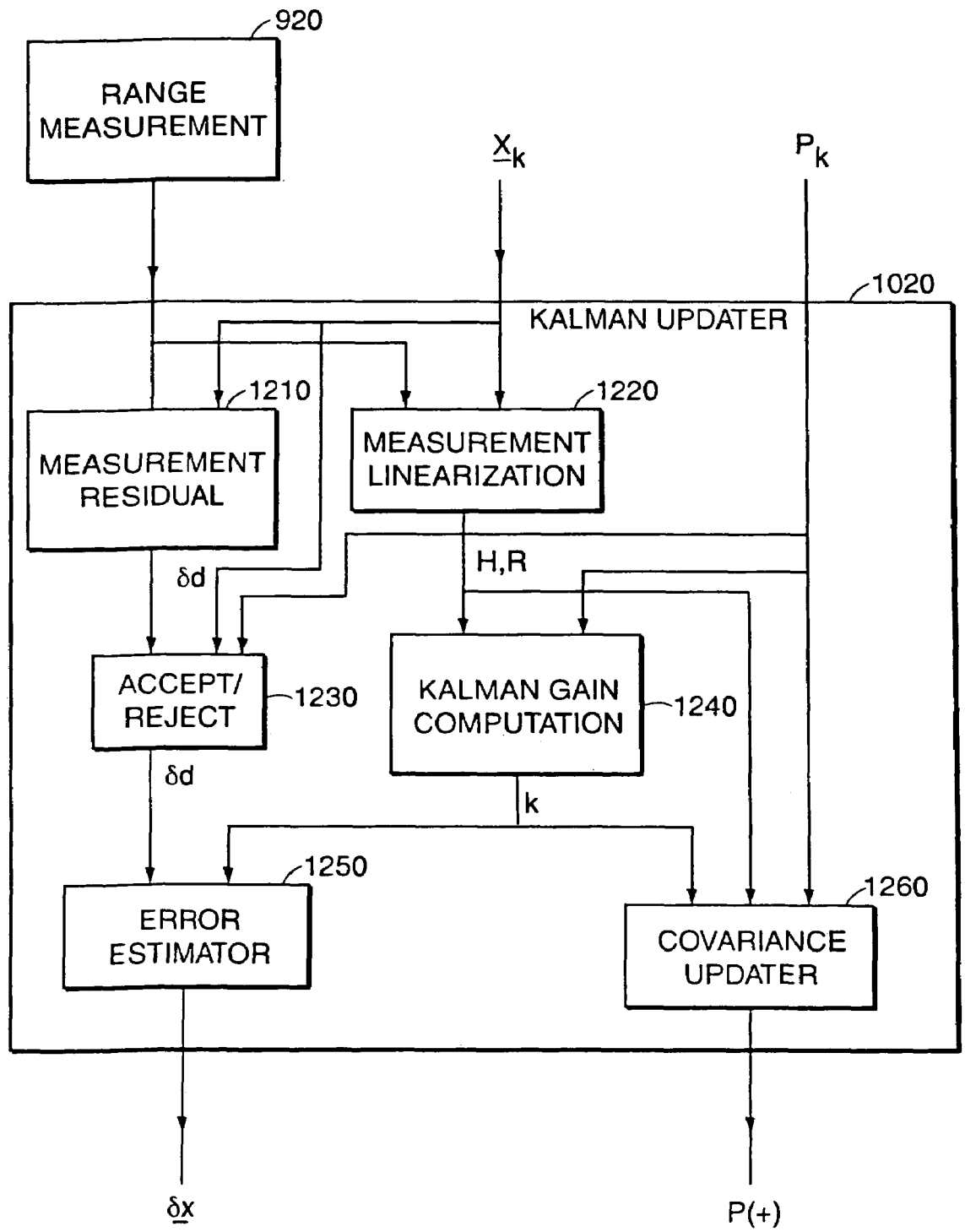
FIG. 12 is a signal flow diagram of a Kalman updater.

Referring to FIG. 12, Kalman updater 1020 accepts the output of range measurement 920, as well as the estimate of location and orientation from inertial tracker 810, and the covariance of the error of the estimate of location and orientation from Kalman predictor 1010, and computes an error estimate, and an updated covariance that results from applying the error estimate. A first stage of Kalman updater 1020 is measurement residual computation 1210. The difference between the expected range and the measured range is computed as $$\delta d_r = d_r - \|\underline{b}^{(n)} - (\underline{r}^{(n)}(t_r) + C_b^n(t_r)\underline{m}^{(b)})\|.$$

Note that in general a range measurement is used some time after it was initially detected. In order to account for this latency, estimates of the location and orientation of the tracking device at the time that the acoustic pulse arrived are used rather than the location and orientation at the time that the measurement is used. The current location, orientation, and linear and angular rate estimates are used to extrapolate back to the measurement time to determine $r^{(n)}(t_r)$ and $C_b^n(t_r)$.

In order to apply the Kalman update equations, this residual is modeled by measurement linearization module 1220 using a linearized observation equation as $$\delta d_r = H(\underline{x}, \underline{b}, d_r, \underline{m})\underline{\delta x} + v.$$

The observation matrix $H_k = H(\underline{x}_k, \underline{b}, d_r, \underline{m})$ is the linear effect of errors in location and orientation on the error in range measurement. The additive noise v has a variance $R(\underline{x}_k, \underline{b}, d_r, \underline{m})$. $H_k$ has the form $$H_k = \left(\frac{b_D m_E - b_E m_D + r_E m_N - r_D m_E}{d_r},\right.$$

$$\frac{b_N m_D - b_D m_N + r_D m_N - r_N m_D}{d_r},$$

$$\frac{b_E m_N - b_N m_E + r_N m_E - r_E m_N}{d_r},$$

$$0, 0, 0, \frac{r_N + m_N - b_N}{d_r}, \frac{r_E + m_E - b_E}{d_r},$$

$$\left.\frac{r_D + m_D - b_D}{d_r}, 0, 0, 0, 0, 0, 0\right)$$

The variance $R(\underline{x}_k, \underline{b}, d_r, \underline{m})$ is derived to model various phenomena associated with ultrasonic range measurement. For example, as the range increases, pulse detection is more difficult, due in part to pulse spreading, and an increased variance is used to model the associated range measurement error. The variance $R(\underline{x}_k, \underline{b}, d_r, \underline{m})$ has the form $$R = \sigma_w^2 + \sigma_1^2$$

and is parameterized as $$\sigma_w^2 = \text{NoiseFloor} + \text{NoiseScaled}_r$$

and $$\sigma_1^2 = (k\Delta t - t_r) H_k (\omega_x, \omega_y, \omega_z, 0, 0, 0, v_x, v_y, v_z, 0, 0, 0, 0, 0))^T$$

The first two terms of $H_k$ can alternatively be set to zero to allow accelerometric tilt correction (if it is more accurate). It the third term is set to zero, yaw drift correction will occur over a longer time period but to higher accuracy.

Kalman updater 1020 includes a measurement accept/reject stage 1230. Accept/reject stage 1230 takes the measurement residual, $\underline{\delta x}$, and the computed variance, R, of the measurement residual. If the measurement residual is greater in magnitude than a predetermined multiple of the computed standard deviation of the measurement residual, then the measurement is rejected as being suspect, for example, due to premature or late triggering of an ultrasonic pulse detector. Otherwise the measurement residual is further processed to compute the state error estimate, $\underline{\delta x}$. Using Kalman filter update equations, Kalman gain computation 1240 computes the Kalman gain as $$K = P_k H_k^T (H_k P_k H_k^T + R)^{-1}.$$

Error estimator 1250 then computes the error estimate as $\underline{\delta x} = K \underline{\delta d}$, and covariance updater 1260 computes the updated error covariance as $$P(+) = (I - KH) P_k.$$

The components of $\underline{\delta x}$ are then used to update inertial tracker 810. The computed terms $\underline{\delta \omega}$ and $\underline{\delta a}^{(b)}$ are passed to gyroscope bias correction 820 and accelerometer bias correction 830 (FIG. 8), respectively, where they are added to the current stored bias parameters. The computed terms and $\underline{\delta v}^{(n)}$ and $\underline{\delta r}^{(n)}$ are passed to double integration 860 (FIG. 8) where they are added to the Current estimates of $\underline{v}^{(n)}$ and $\underline{r}^{(n)}$, respectively. Finally, the direction cosine matrix is updated according to $$C_k - (I - S(\underline{\phi})) C_k$$

and re-orthonormalized.

Referring back to FIG. 1, ultrasonic beacon array 120 includes individual ultrasonic beacons 122 arranged in a regular pattern. For example, the beacons may be arranged 20 on a square grid with a spacing of approximately 2 feet, preferably with an accuracy of 3 mm or less. A limited number of addresses are available for the beacons, in this embodiment only eight different addresses are available due to hardware limitations. Therefore, when the tracking device sends an IR command to an address, in general, multiple ultrasonic beacons will receive the signal and respond. Only the closest beacon with any particular address is used for range measurement. However, as multiple beacons may be responding to each IR command, the pulse detection circuit may be triggered prematurely, for example, by a pulse from a beacon triggered in a previous iteration, but that is sufficiently far away that its pulse does not arrive until after a subsequent iteration. In order to avoid this pre-triggering problem, pulse detector 522 (FIG. 5) is only enabled during a time window about the expected time the desired pulse would arrive. This avoids false triggering by pulses from other beacons, or signals resulting from long time constant reverberation of previous pulses.

In the description the tracking and Kalman updating procedures, an initial location and orientation estimate is assumed to be known. This is not necessarily the case and an automatic acquisition algorithm is used by tracking device 100. The limited number of addresses of ultrasonic beacons is used as the basis for an initial acquisition algorithm. Initially, the tracking device triggers beacons with each of the allowable addresses and measures the range to the closest beacon of each address. Then, the addresses of the four closest beacons are determined from the range measurements. The tracking unit includes a beacon map that includes the locations and addresses of all the beacons. The beacons are arranged such that the addresses of the four closest beacons limit the possible locations to a small portion of the room. If there is ambiguity based on the closest beacons, the actual distances to the beacons are used in a triangulation procedure to resolve the ambiguity. The initial orientation is based on the relative range measurements to each of the microphones.

Figure 13:
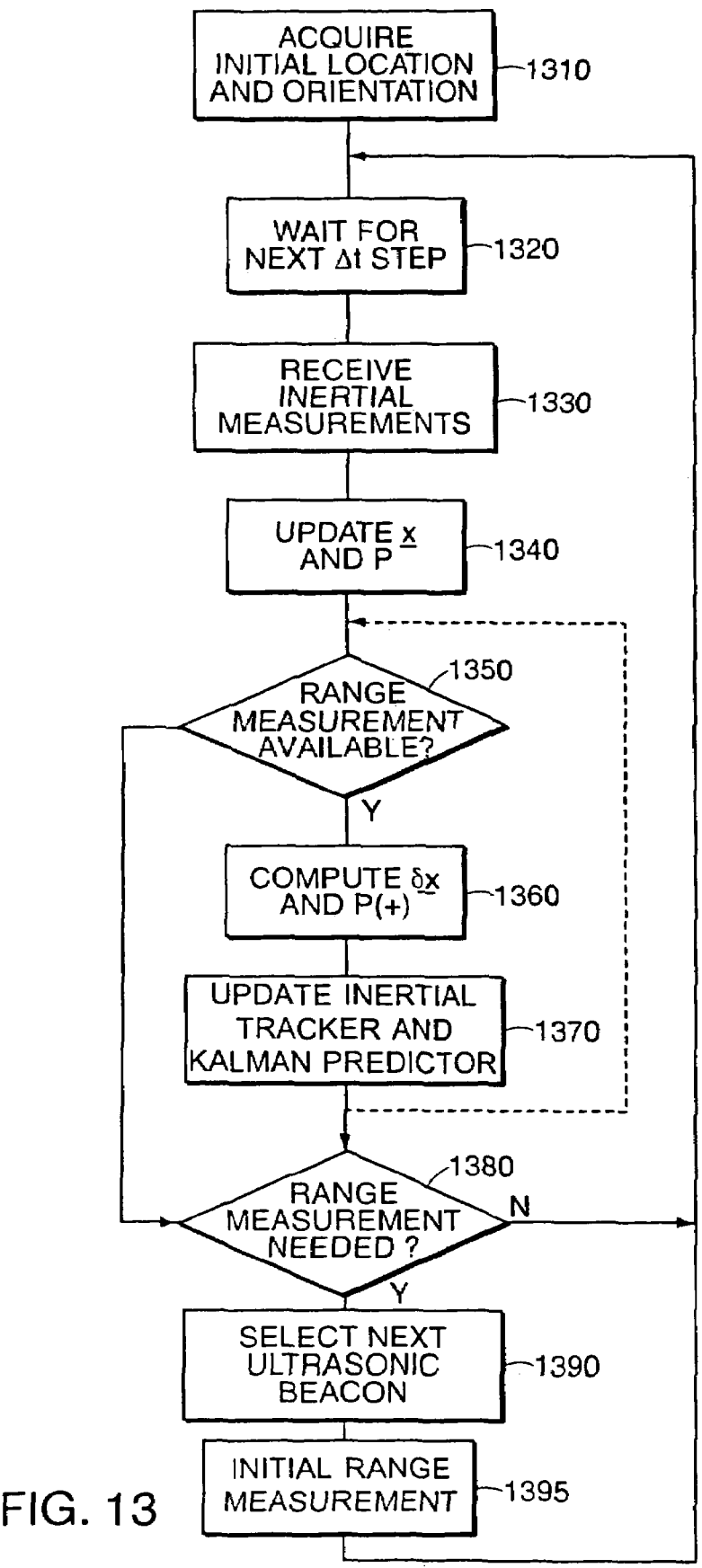
FIG. 13 is a flowchart of a tracking procedure.

The overall tracking procedure can be summarized by the flowchart shown in FIG. 13. First, the initial location and orientation is acquired (step 1310) using the approach outlined above. The procedure then enters a loop that is executed once each time step. After waiting for the next time step (step 1320), inertial measurements are received (step 1330) and the tracked variables, x, and the error covariance, P, are updated using the inertial measurements (step 1340). If an ultrasonic range measurement that has not yet been processed is available (step 1350), that range measurement is used to compute an error update, $\underline{\delta x}$, and updated error covariance, P(+), (step 1360). The error update and new error covariance are then used to update the inertial tracker and the Kalman predictor (step 1370). The procedure then involves determining whether further range measurements must be commanded at this time step (step 1380). As three range measurements are made for each pulse but only one range measurement is used per time step, there may be a backlog of range measurements that will be applied in the upcoming time steps. Therefore, a new range measurement may not be necessarily for several future time steps. Taking into account the expected time of flight of the next ultrasonic pulse (which in general is more than a single time step), the procedure determines if an IR command should be sent to a beacon at this time step (step 1380), the next beacon address is selected (step 1390) and, if so, the IR command to that beacon is sent (step 1395). The procedure then loops again starting at step 1320, waiting for the start of the next time interval.

Several alternative approaches can also be used. In the described embodiment, only one range measurement is used per time step. Alternatively, all available range measurements can be used at each time step if the processor 130 has sufficient computation capacity. This alternative approach is implemented by looping from step 1370 back to step 1350 until all the range measurements are accounted for. Alternatively, rather than applying the Kalman updates for each of the scalar range measurements in turn, all can be applied in a single step using similar update equations for vector observations and correlated observation noise. Also, rather than deferring processing of a range measurement until the next time step, the range measurements can be incorporated as they arrive, and not synchronized with the inertial tracker updates.

The procedure described above can be combined with other measurement modes. For example, inclinometers can be used to provide measurements to the extended Kalman filter that allow correction of attitude drift. Also, rather than using three or more microphones which allow correction of all three degrees of rotation, two microphones can be used for range measurement in combination with a measurement mode such as inclinometers. In this way, some drift correction can be based on inclinometers, but a compass, which is sensitive to magnetic field variations, is not needed for drift correction. Many more than three microphones can also be used to provide greater redundancy and allow more rotation freedom.

As an alternative to mounting beacons in fixed locations in the environment, and microphones on the tracking device, which is often referred to as an "inside-out" arrangement, this could be reversed in an "outside-in" arrangement. The tracking device then provides the ultrasonic pulses and a coordinated array of microphones senses the location of the tracking device. Note that by the time a pulse has reached a microphone, the tracking device will have, in general, moved on to a new location. This latency of measurements must be compensated for in a manner similar to the compensation of latency in use of range measurements described above.

Beacons 122 need not be mounted in a planar array. They could be mounted on walls as well as on the ceiling, or on other supports in the environment. For example, the beacons can be mounted on light fixtures. The number of beacons can be chosen to match the user's requirements, and the locations of the beacons can be chosen based on a variety of criterea, such as availability of suitable mounting points and geometric considerations, and the beacon map can be set to match the chosen number and locations of the beacons. The number of beacons in the constellation can be increased or reduced by the user, so long as the beacon map remains up to date.

The command signals from the tracking device to the beacons can be sent using other modes than IR transmission. For example, RF, visible, or acoustic signals can be used. The tracking device can also be wired to the beacons.

Figure 14A:
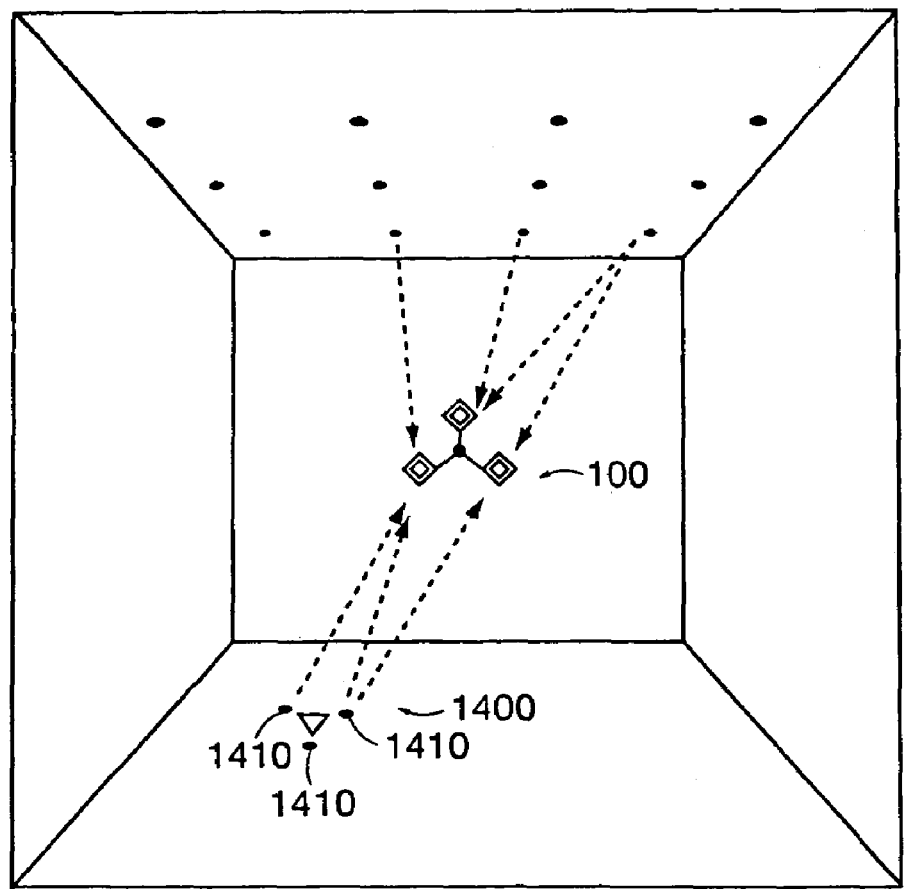
FIG. 14a illustrates tracking of a second body relative to a first tracked body.

Two or more objects can be tracked in an "inside-outside-in" arrangement. Referring to FIG. 14a, tracking device 100 tracks its location as before. A second tracking device 1400 includes three addressable ultrasonic beacons 1410 arranged in a known relationship to one another. By triggering beacons 1410 to transmit acoustic pulses that are received at the URM 110 on tracking device 100, tracking device can determine the relative location and orientation of the second tracking device. A further extension, which provides increased accuracy in the relative location and orientation estimates involves having a second inertial measurement unit fixed to tracking device 1400, and transmitting its inertial measurements to tracking device 100. If only a single beacon is placed on the second object, the relative location can be sensed using ultrasonic range measurements, without necessarily tracking the relative orientation of the second device.

Figure 14B:
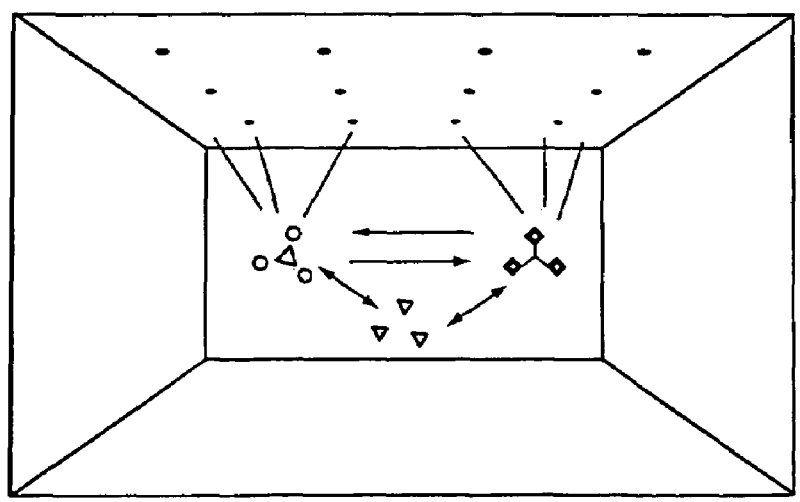
FIG. 14b illustrates mutual tracking of multiple devices.

Referring to FIG. 14b, a "mutual tracking network" made up of multiple tracking devices can be used. These tracking devices track their individual locations with respect to the locations of the other devices in the environment, including fixed beacons and other moving tracked objects. This can be done with an additional communication system coupling the tracking devices, such as an RF local area network.

In the above described embodiments, the "map" of the beacon array is assumed to be accurate. As the range measurements include redundant information, errors in placement of the beacons can be iteratively estimated and updated, thereby improving accuracy. Specifically, the placement errors of the beacons can be included in the state of the extended Kalman filter, and range measurements from each beacon would then contribute over time to estimating the placement errors. A separate initial automatic "mapping" mode can also be used in which, through range measurement from one or more locations in the room and triangulation calculations, the locations of the beacons can be determined. These automatically determined locations can be used as the known locations, or as initial estimates that are then further updated using the Kalman filter. In this type of approach, the beacons can be irregularly placed within the room without requiring that they be precisely positioned.

Figure 15:
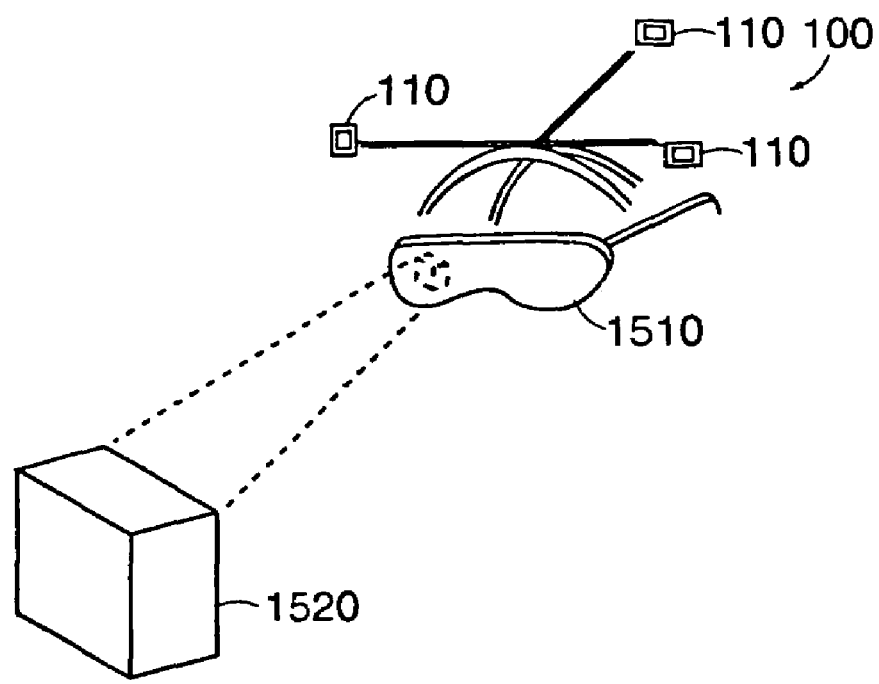
FIG. 15 illustrates head mounted display system.

The tracking approach described above has several applications. A first application involves coupling the tracking device to a head mounted display. Referring to FIG. 15, a head mounted display 1510, allows a user to directly view a physical object 1520, such as a work piece. Display 1510, using the known location of work piece 1520 in the frame of reference of the room, superimposes information on the user's view of the work piece. For example, applying wiring harnesses to a large device, the superimposed information can include information related to the correct placement of the wiring harnesses. A similar head mounted display can also be used to provide the complete image viewed by a user in a virtual reality system, rather than superimposing an image on the real view seen by the user.

Figure 16:
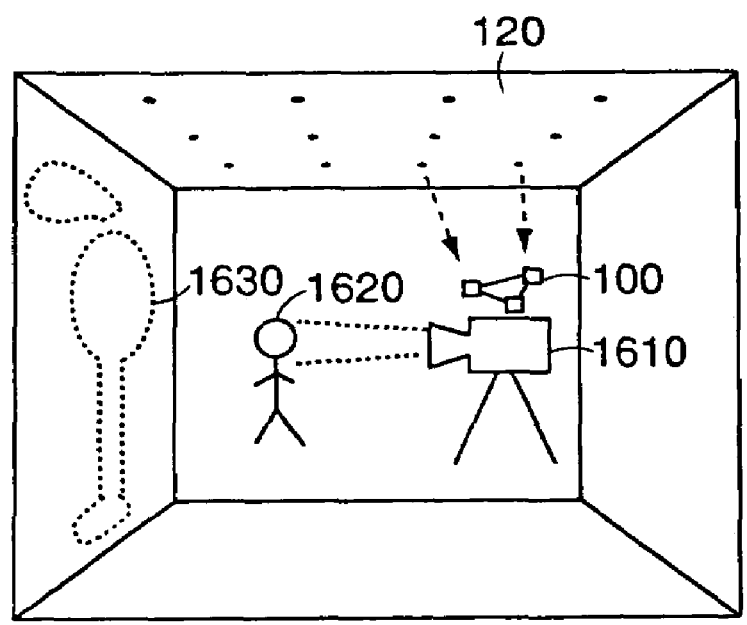
FIG. 16 illustrates a camera tracking system for television.

Another application involves tracking a camera location in a television application. Referring to FIG. 16, a common technique in television production is to film a subject 1620 in front of a blank (typically monochrome) background and then to electronically superimpose another image (illustrated as 1630) as a background. A difficulty with such a technique is that as camera 1610 moves, the background image should change to reflect the camera's motion. By attaching tracking device 100 to camera 1610, the location and orientation of the camera is tracked and the background image can be automatically modified by an image processor that receives the changing position and orientation of the camera. This approach allows construction of large "virtual sets" which are stored in the image processor, and thereby multiple and changing camera "angles" can be used.

Figure 17:
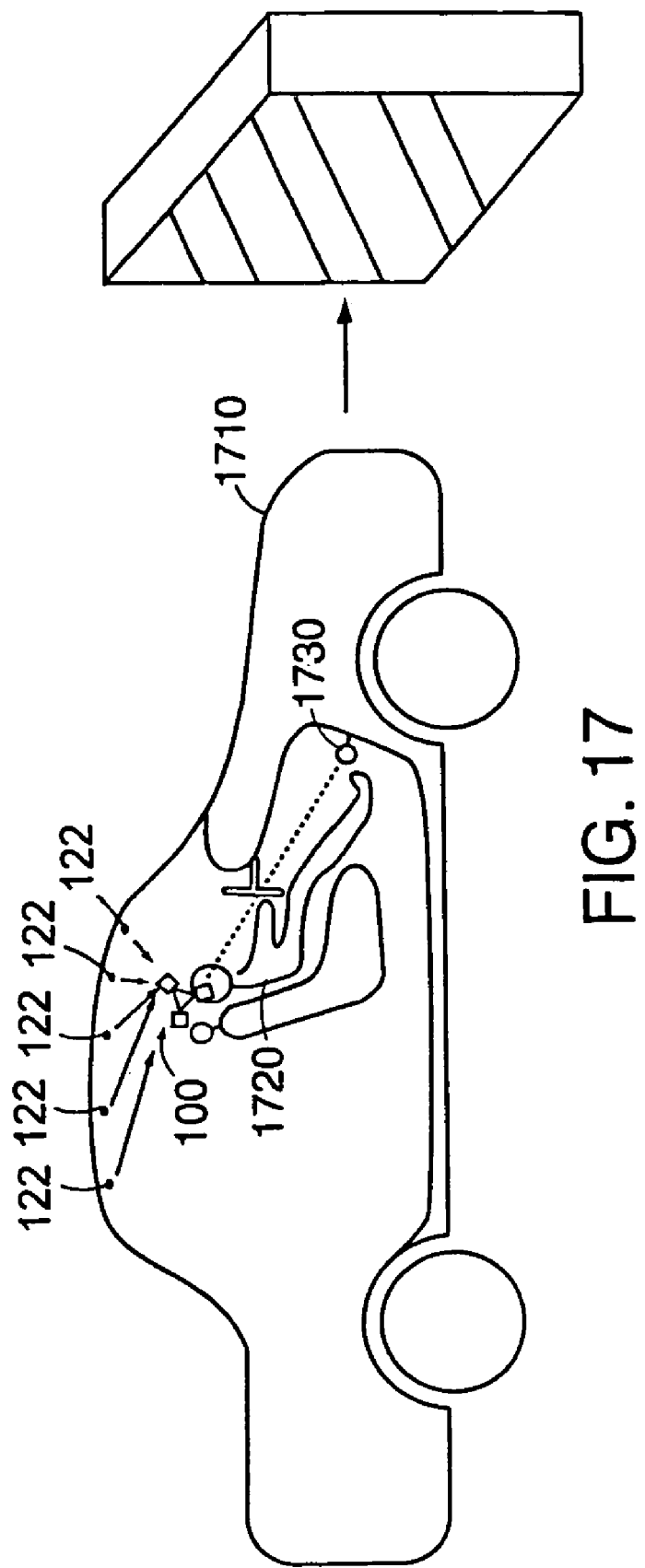
FIG. 17 illustrates tracking of bodies in an automobile.

Another application involves sensing of motion of elements in an automobile, for example, in an automotive crash test. Referring to FIG. 17, the motion of a dummy 1720 within a crashing automobile 1710 can be tracked using tracking device 100. In addition, a second object., such as a point on the firewall can be tracked using an addition beacon 1730 using the inside-outside-in approach described above. This allows both tracking of the dummy in the reference frame of the automobile, and tracking of a point within the vehicle relative to the dummy.

Other applications include robotic navigation, tracking of inventory, assets, or personnel, shipboard virtual or augmented reality for damage control, film camera tracking, entertainment (e.g., theme parks and games), full body tracking for motion capture, and weapon tracking.

Alternative embodiments can also use other approaches to inertial tracking. For example, rather than performing attitude integration using a direction cosine matrix, attitude integration using Euler angles or quaternions can equivalently be used. Note that the linearized error propagation system matrix and driving noise covariance may depend somewhat on the particular tracking algorithm used. Also, the state of the Kalman filter can be changed, for instance, to include other terms. One example of this is to not only track accelerometer additive bias, as in the embodiments described above, but also to track multiplicative bias (e.g., error in scale factor) of the accelerometer signal, misalignment, and the speed of sound.

Other methods of range measurement can also be used, including acoustic phase, RF or optical time of flight, RF or optical phase, and mechanical cable extension.

Other methods of fusing inertial and acoustic measurements can be used instead of Kalman filtering. For example, neural network, rule-based reasoning, or fuzzy logic systems, or optimization methods, can be used to combine the measurements.

In the description above, only eight different ultrasonic beacon addresses are used. Alternatively, each beacon can be individually addressable, or a larger number of shared addresses can be used. If the beacons are individually addressable, initial acquisition can be performed, for example, by having beacons also respond to "group" addresses, or to sequence commands addressed to individual beacons during the acquisition phase in such a way that tracking device can "zero in" to its initial location by first finding one beacon that is in range, and then searching for additional beacons that are closer and closer based on the beacon map known to the tracking device. Such an approach can also be used when the tracking area is made up of several different rooms. Initially, the room that the tracking device is in is determined and then the location within the room can be found.

It is to be understood that the foregoing description is intended to illustrate and not limit the scope of the invention, which is defined by the scope of the appended claims. Other aspects, advantages, and modifications are within the scope of the following claims.

What is claimed is:

1. A method for tracking the motion of a body including:
obtaining an inertial measurement;
updating a state estimate of the body by integrating the inertial measurement;
updating an estimate of an uncertainty of the state estimate, including using a rate estimate of the body to increase the estimate of the uncertainty of the state estimate such that the uncertainty of the state estimate increases at relatively greater rate during time periods with high rate estimates.

2. The method of claim 1 wherein the inertial measurement is associated with a rate of the body.

3. The method of claim 2 wherein the inertial measurement is associated with an angular rate of the body.

4. The method of claim 3 wherein the inertial measurement includes an angular acceleration measurement.

5. The method of claim 2 wherein the inertial measurement is associated with a linear rate of the body.

6. The method of claim 5 wherein the inertial measurement includes a linear acceleration measurement.

7. The method of claim 1 wherein the state estimate of the body includes a position estimate of the body.

8. The method of claim 1 wherein the rate estimate includes an angular rate estimate.

9. The method of claim 1 wherein updating the state estimate and updating the estimate of the uncertainty of the state estimate are performed according to a linear stochastic system model.

10. The method of claim 9 wherein updating the state estimate and updating the estimate of the uncertainty of the state estimate are performed according to a Kalman Filtering approach.

11. The method of claim 9 wherein the uncertainty of the state estimate is represented by data including a covariance matrix $P_k$.

12. The method of claim 11 wherein updating the uncertainty of the state estimate includes applying an updating approach equivalent to updating a previous estimate of uncertainty of the state estimate, $P_{k-1}$ according to an equation $P_k = F P_{k-1} F' + Q$ where at least some of the entries of a matrix Q depend on the rate estimate of the body.

13. The method of claim 12 wherein the matrix Q represents a covariance of a process noise for the evolution of the state of the body.

14. The method of claim 12 wherein the inertial measurement is associated with an angular rate of the body the inertial measurement and at least some of the entries of the matrix Q depend an angular rate estimate.

15. The method of claim 14 wherein at least some of the entries of the matrix Q include terms that are proportional to the angular rate measurement.

* * * * *

UNITED STATES PATENT AND TRADEMARK OFFICE
CERTIFICATE OF CORRECTION

PATENT NO. : 7,395,181 B2
APPLICATION NO. : 10/747392
DATED : July 1, 2008
INVENTOR(S) : Eric Foxlin It is certified that error appears in the above-identified patent and that said Letters Patent is hereby corrected as shown below:

<u>Title Page: item 56 Other Publications</u>
Col. 2, Foxlin et al., reference, Delete ""Minature" insert --"Miniature--.
Col. 2, Foxlin et al., reference, Delete "TRacking" insert --Tracking--.

<u>Page 26</u>
Col. 16,
Claim 14, Line 25, Delete "body" insert --body,--.
Claim 14, Line 27, Delete "depend an" insert --depends on--.

Signed and Sealed this

Twenty-third Day of September, 2008

JON W. DUDAS
*Director of the United States Patent and Trademark Office*